(12) United States Patent
Luk et al.

(10) Patent No.: US 11,110,093 B2
(45) Date of Patent: *Sep. 7, 2021

(54) SUSTAINED RELEASE SMALL MOLECULE DRUG FORMULATION

(71) Applicant: INDIVIOR UK LIMITED, Hull (GB)

(72) Inventors: Andrew S. Luk, Castro Valley, CA (US); Gunjan H. Junnarkar, Palo Alto, CA (US); Guohua Chen, Sunnyvale, CA (US)

(73) Assignee: INDIVIOR UK LIMITED, Hull (GB)

( * ) Notice: Subject to any disclaimer, the term of this patent is extended or adjusted under 35 U.S.C. 154(b) by 40 days.

This patent is subject to a terminal disclaimer.

(21) Appl. No.: 16/511,210

(22) Filed: Jul. 15, 2019

(65) Prior Publication Data

US 2020/0046704 A1 Feb. 13, 2020

Related U.S. Application Data

(63) Continuation of application No. 16/044,259, filed on Jul. 24, 2018, now Pat. No. 10,406,160, which is a continuation of application No. 15/422,626, filed on Feb. 2, 2017, now Pat. No. 10,058,554, which is a continuation of application No. 14/701,173, filed on Apr. 30, 2015, now Pat. No. 9,597,402, which is a continuation of application No. 13/790,930, filed on Mar. 8, 2013, now Pat. No. 9,044,450, which is a continuation of application No. 11/535,398, filed on Sep. 26, 2006, now Pat. No. 8,852,638.

(60) Provisional application No. 60/722,845, filed on Sep. 30, 2005.

(51) Int. Cl.
| | |
|---|---|
| *A61K 9/14* | (2006.01) |
| *A61K 31/519* | (2006.01) |
| *A61K 51/12* | (2006.01) |
| *A61K 9/06* | (2006.01) |
| *A61K 9/00* | (2006.01) |
| *A61K 47/10* | (2017.01) |
| *A61K 47/14* | (2017.01) |
| *A61K 47/22* | (2006.01) |
| *A61K 47/34* | (2017.01) |
| *A61K 31/341* | (2006.01) |
| *A61K 9/16* | (2006.01) |

(52) U.S. Cl.
CPC .......... *A61K 31/519* (2013.01); *A61K 9/0019* (2013.01); *A61K 9/0024* (2013.01); *A61K 9/06* (2013.01); *A61K 9/1617* (2013.01); *A61K 9/1647* (2013.01); *A61K 31/341* (2013.01); *A61K 47/10* (2013.01); *A61K 47/14* (2013.01); *A61K 47/22* (2013.01); *A61K 47/34* (2013.01); *A61K 51/1213* (2013.01)

(58) Field of Classification Search
CPC .............................. A61K 9/06; A61K 51/1213
See application file for complete search history.

(56) References Cited

U.S. PATENT DOCUMENTS

| | | |
|---|---|---|
| 3,466,362 A | 9/1969 | Klaui et al. |
| 4,530,840 A | 7/1985 | Tice et al. |
| 4,534,974 A | 8/1985 | Kim |
| 4,573,995 A | 3/1986 | Chen et al. |
| 4,622,219 A | 11/1986 | Haynes |
| 4,626,539 A | 12/1986 | Aungst et al. |
| 4,725,442 A | 2/1988 | Haynes |
| 4,755,389 A | 7/1988 | Jones et al. |
| 4,767,628 A | 8/1988 | Hutchinson |
| 4,784,855 A | 11/1988 | Yamashita et al. |
| 4,804,663 A | 2/1989 | Kennis et al. |
| 4,891,225 A | 1/1990 | Langer et al. |
| 4,906,474 A | 3/1990 | Langer et al. |
| 4,938,763 A | 7/1990 | Dunn et al. |
| 4,957,744 A | 9/1990 | Valle et al. |
| 5,008,110 A | 4/1991 | Benecke et al. |
| 5,026,556 A | 6/1991 | Drust et al. |
| 5,069,909 A | 12/1991 | Sharma et al. |
| 5,096,715 A | 3/1992 | Sinclair |
| 5,149,543 A | 9/1992 | Cohen et al. |
| 5,173,304 A | 12/1992 | Lohner et al. |
| 5,278,201 A | 1/1994 | Dunn et al. |
| 5,324,519 A | 6/1994 | Dunn et al. |
| 5,453,425 A | 9/1995 | Francois et al. |
| 5,534,269 A | 7/1996 | Igari et al. |

(Continued)

FOREIGN PATENT DOCUMENTS

| | | |
|---|---|---|
| CA | 2666341 A1 | 4/2008 |
| EP | 0368409 A2 | 5/1990 |

(Continued)

OTHER PUBLICATIONS

Kan, P. et al, "Thermogelling Emulsions for Vascular Embolization and Sustained Release Drugs", Journal of Biomedical Materials Research, 75B(1):185-192 (Jul. 21, 2005).

(Continued)

*Primary Examiner* — James W Rogers
(74) *Attorney, Agent, or Firm* — Lisa E. Stahl; Kathryn Jones

(57) ABSTRACT

An injectable depot formulation includes a biocompatible polymer, an organic solvent combined with the biocompatible polymer to form a viscous gel, and a small molecule drug incorporated in the viscous gel such that the formulation exhibits an in vivo release profile having a $C_{max}$ to $C_{min}$ ratio of less than 200 and a lag time less than 0.2.

20 Claims, 2 Drawing Sheets

(56) References Cited

U.S. PATENT DOCUMENTS

| | | |
|---|---|---|
| 5,612,346 A | 3/1997 | Mesens et al. |
| 5,616,587 A | 4/1997 | François et al. |
| 5,643,605 A | 7/1997 | Cleland et al. |
| 5,648,093 A | 7/1997 | Gole et al. |
| 5,656,299 A | 8/1997 | Kino et al. |
| 5,688,801 A | 11/1997 | Mesens et al. |
| 5,702,716 A | 12/1997 | Dunn et al. |
| 5,723,467 A | 3/1998 | Mesens et al. |
| 5,744,153 A | 4/1998 | Yewey et al. |
| 5,747,058 A | 5/1998 | Tipton et al. |
| 5,770,231 A | 6/1998 | Mesens et al. |
| 5,780,044 A | 7/1998 | Yewey et al. |
| 5,792,477 A | 8/1998 | Rickey et al. |
| 5,871,778 A | 2/1999 | Kino et al. |
| 5,916,598 A | 6/1999 | Rickey et al. |
| 5,945,115 A | 8/1999 | Dunn et al. |
| 5,965,168 A | 10/1999 | Mesens et al. |
| 5,968,542 A | 10/1999 | Tipton |
| 5,990,194 A | 11/1999 | Dunn et al. |
| 6,004,969 A | 12/1999 | Hu |
| 6,110,503 A | 8/2000 | Rickey et al. |
| 6,110,921 A | 8/2000 | Mesens et al. |
| 6,120,789 A | 9/2000 | Dunn |
| 6,130,200 A | 10/2000 | Brodbeck et al. |
| 6,143,314 A | 11/2000 | Chandrashekar et al. |
| 6,194,006 B1 | 2/2001 | Lyons et al. |
| 6,224,905 B1 | 5/2001 | Lawrence et al. |
| 6,261,583 B1 | 7/2001 | Dunn et al. |
| 6,264,987 B1 | 7/2001 | Wright et al. |
| 6,284,274 B1 | 9/2001 | Merrill et al. |
| 6,290,983 B1 | 9/2001 | Rickey et al. |
| 6,291,013 B1 | 9/2001 | Gibson et al. |
| 6,294,192 B1 | 9/2001 | Patel et al. |
| 6,303,137 B1 | 10/2001 | Dittgen et al. |
| 6,331,311 B1 | 12/2001 | Brodbeck et al. |
| 6,355,657 B1 | 3/2002 | Osborne |
| 6,368,632 B1 | 4/2002 | Mesens et al. |
| 6,379,703 B1 | 4/2002 | Lyons et al. |
| 6,379,704 B2 | 4/2002 | Wright et al. |
| 6,383,471 B1 | 5/2002 | Chen et al. |
| 6,395,293 B2 | 5/2002 | Polson et al. |
| 6,403,114 B1 | 6/2002 | Rickey et al. |
| 6,413,536 B1 | 7/2002 | Gibson et al. |
| 6,431,536 B1 | 8/2002 | Maffeis |
| 6,438,961 B2 | 8/2002 | Tuthill et al. |
| 6,461,631 B1 | 10/2002 | Dunn et al. |
| 6,468,961 B1 | 10/2002 | Brodbeck et al. |
| 6,528,080 B2 | 3/2003 | Dunn et al. |
| 6,534,092 B2 | 3/2003 | Wright et al. |
| 6,565,874 B1 | 5/2003 | Dunn et al. |
| 6,596,316 B2 | 7/2003 | Lyons et al. |
| 6,622,036 B1 | 9/2003 | Suffin |
| 6,630,155 B1 | 10/2003 | Chandrashekar et al. |
| 6,667,061 B2 | 12/2003 | Ramstack et al. |
| 6,673,767 B1 | 1/2004 | Brodbeck et al. |
| 6,750,341 B2 | 6/2004 | Krochmal et al. |
| 6,897,308 B1 | 5/2005 | Venkatasubramanian et al. |
| 6,956,059 B2 | 10/2005 | Coupland |
| 7,041,320 B1 | 5/2006 | Nuwayser |
| RE39,181 E | 7/2006 | François et al. |
| 7,118,763 B2 | 10/2006 | Mesens et al. |
| 7,202,360 B2 | 4/2007 | Kim et al. |
| 7,410,635 B2 | 8/2008 | Blondino et al. |
| 7,501,113 B2 | 3/2009 | Blondino et al. |
| 7,691,408 B2 | 4/2010 | Leroux et al. |
| 7,820,202 B2 | 10/2010 | Bodmeier |
| 7,824,700 B2 | 11/2010 | Cleland et al. |
| 7,833,543 B2 | 11/2010 | Gibson et al. |
| 7,927,618 B2 | 4/2011 | Bodmeier |
| 8,114,383 B2 | 2/2012 | Bartholomäus et al. |
| 8,114,429 B2 | 2/2012 | Michal et al. |
| 8,133,507 B2 | 3/2012 | Yum et al. |
| 8,173,148 B2 | 5/2012 | Dadey et al. |
| 8,221,778 B2 | 7/2012 | Siegel et al. |
| 8,236,755 B2 | 8/2012 | Thuresson et al. |
| 8,257,722 B2 | 9/2012 | Michal et al. |
| 8,313,763 B2 | 11/2012 | Margaron et al. |
| 8,324,343 B2 | 12/2012 | Moore et al. |
| 8,329,203 B2 | 12/2012 | Siegel et al. |
| 8,333,989 B2 | 12/2012 | Sukuru |
| 8,377,479 B2 | 2/2013 | Talton |
| 8,415,401 B2 | 4/2013 | Yum et al. |
| 8,486,455 B2 | 7/2013 | Dunn et al. |
| 8,501,216 B2 | 8/2013 | Cleland et al. |
| 8,512,749 B2 | 8/2013 | Sawhney et al. |
| 8,563,023 B2 | 10/2013 | Michal et al. |
| 8,574,552 B2 | 11/2013 | Stroppolo et al. |
| 8,586,103 B2 | 11/2013 | Li et al. |
| 8,741,327 B2 | 6/2014 | Siegel et al. |
| 8,802,127 B2 | 8/2014 | Siegel et al. |
| 8,815,944 B2 | 8/2014 | Leroux et al. |
| 8,852,638 B2 | 10/2014 | Luk et al. |
| 8,877,225 B2 | 11/2014 | Norton et al. |
| 8,877,241 B2 | 11/2014 | Fischer et al. |
| 8,916,202 B2 | 12/2014 | Lebon et al. |
| 9,017,709 B2 | 4/2015 | Griguol et al. |
| 9,044,450 B2 | 6/2015 | Luk et al. |
| 9,168,216 B2 | 10/2015 | Gavin et al. |
| 9,180,197 B2 | 11/2015 | Dadey |
| 9,186,413 B2 | 11/2015 | Dadey |
| 9,221,831 B2 | 12/2015 | Kyle et al. |
| 9,254,268 B2 | 2/2016 | Krayz et al. |
| 9,259,872 B2 | 2/2016 | Hayes et al. |
| 9,308,162 B2 | 4/2016 | Norton |
| 9,326,979 B2 | 5/2016 | Kimura et al. |
| 9,364,518 B2 | 6/2016 | Nadkarni et al. |
| 9,415,034 B2 | 8/2016 | Oliver et al. |
| 9,439,905 B2 | 9/2016 | Siegel et al. |
| 9,468,599 B2 | 10/2016 | Ray et al. |
| 9,555,226 B2 | 1/2017 | Zumbrunn et al. |
| 9,597,402 B2 | 3/2017 | Luk et al. |
| 9,717,799 B2 | 8/2017 | Siegel et al. |
| 10,010,612 B2 | 7/2018 | Dadey et al. |
| 10,376,590 B2 | 8/2019 | Dadey et al. |
| 10,406,160 B2 | 9/2019 | Luk et al. |
| 2002/0064547 A1 | 5/2002 | Chern et al. |
| 2002/0098233 A1* | 7/2002 | Mesens ............. A61P 43/00 424/462 |
| 2003/0004100 A1 | 1/2003 | Dasch et al. |
| 2003/0009145 A1 | 1/2003 | Struijker-Boudier et al. |
| 2003/0068375 A1 | 4/2003 | Wright et al. |
| 2003/0129219 A1 | 7/2003 | Hong et al. |
| 2004/0018238 A1 | 1/2004 | Shukla |
| 2004/0101557 A1 | 5/2004 | Gibson et al. |
| 2004/0138237 A1 | 7/2004 | Shah |
| 2004/0258731 A1 | 12/2004 | Shimoboji et al. |
| 2005/0032781 A1 | 2/2005 | Ehrich |
| 2005/0048123 A1 | 3/2005 | Su et al. |
| 2005/0053647 A1 | 3/2005 | Matusch et al. |
| 2005/0112067 A1 | 5/2005 | Kumar et al. |
| 2006/0002979 A1 | 1/2006 | Ashammakhi et al. |
| 2006/0003008 A1 | 1/2006 | Gibson et al. |
| 2007/0077304 A1 | 4/2007 | Luk et al. |
| 2007/0108405 A1 | 5/2007 | Khoo et al. |
| 2007/0196416 A1 | 8/2007 | Li et al. |
| 2008/0020011 A1 | 1/2008 | Finkelstein et al. |
| 2008/0020039 A1 | 1/2008 | Parikh et al. |
| 2008/0287464 A1 | 11/2008 | Wright et al. |
| 2008/0299168 A1 | 12/2008 | Dadey et al. |
| 2009/0048145 A1 | 2/2009 | Hellerbrand et al. |
| 2009/0074708 A1 | 3/2009 | Oliver et al. |
| 2009/0092650 A1 | 4/2009 | Warren et al. |
| 2009/0202481 A1 | 8/2009 | Li et al. |
| 2009/0246265 A1 | 10/2009 | Stinchcomb et al. |
| 2009/0325879 A1 | 12/2009 | Norton et al. |
| 2010/0098735 A1 | 4/2010 | Jain et al. |
| 2010/0173940 A1 | 7/2010 | Leichs et al. |
| 2010/0266655 A1 | 10/2010 | Dadey |
| 2010/0292195 A1 | 11/2010 | Dadey et al. |
| 2010/0330150 A1 | 12/2010 | Venkatesh et al. |
| 2011/0229526 A1 | 9/2011 | Rosenberg et al. |
| 2011/0230816 A1 | 9/2011 | Copp-Howland |
| 2011/0245172 A1 | 10/2011 | Norton |
| 2012/0058158 A1 | 3/2012 | Booles |

(56) References Cited

U.S. PATENT DOCUMENTS

| | | |
|---|---|---|
| 2012/0207843 A1 | 8/2012 | Lebon et al. |
| 2013/0023553 A1 | 1/2013 | Jude-Fishburn et al. |
| 2013/0129828 A1 | 5/2013 | Talton |
| 2013/0143909 A1 | 6/2013 | Chong et al. |
| 2013/0171202 A1 | 7/2013 | Aduriz et al. |
| 2013/0177603 A1 | 7/2013 | Aduriz et al. |
| 2013/0210751 A1 | 8/2013 | Dong et al. |
| 2013/0231359 A1 | 9/2013 | Chong et al. |
| 2013/0289053 A1 | 10/2013 | Wright et al. |
| 2013/0331803 A1 | 12/2013 | Fleschhut et al. |
| 2014/0023692 A1 | 1/2014 | Toit et al. |
| 2014/0134261 A1 | 5/2014 | Singh et al. |
| 2014/0271869 A1 | 9/2014 | Richey et al. |
| 2014/0308352 A1 | 10/2014 | Wright et al. |
| 2014/0363487 A1 | 12/2014 | Hille et al. |
| 2015/0005323 A1 | 1/2015 | Dadey |
| 2015/0099767 A1 | 4/2015 | Dadey |
| 2015/0209555 A1 | 7/2015 | Ruane et al. |
| 2015/0231258 A1 | 8/2015 | Luk et al. |
| 2015/0250738 A1 | 9/2015 | Yum et al. |
| 2015/0359891 A1 | 12/2015 | Chen et al. |
| 2016/0106847 A1 | 4/2016 | Dadey et al. |
| 2016/0303038 A1 | 10/2016 | Yadav et al. |
| 2017/0239252 A1 | 8/2017 | Luk et al. |

FOREIGN PATENT DOCUMENTS

| | | |
|---|---|---|
| EP | 0368409 A3 | 12/1990 |
| EP | 0730865 A1 | 9/1996 |
| EP | 0537559 B1 | 1/1998 |
| EP | 0532546 B1 | 3/1998 |
| EP | 0572494 B1 | 8/1999 |
| EP | 0998917 A1 | 5/2000 |
| EP | 1006935 A1 | 6/2000 |
| EP | 1015032 A2 | 7/2000 |
| EP | 1210942 A2 | 6/2002 |
| EP | 1210942 A3 | 5/2004 |
| EP | 1181935 B1 | 9/2005 |
| EP | 1649850 A1 | 4/2006 |
| EP | 1317254 B1 | 2/2007 |
| EP | 1248596 B1 | 3/2007 |
| EP | 1830900 A1 | 9/2007 |
| EP | 2081574 A1 | 7/2009 |
| EP | 1644002 B1 | 12/2009 |
| EP | 1940351 B1 | 4/2012 |
| EP | 2445487 A2 | 5/2012 |
| EP | 2529756 A2 | 12/2012 |
| EP | 2361609 B1 | 7/2013 |
| EP | 2529756 A3 | 8/2013 |
| EP | 2797602 A2 | 11/2014 |
| EP | 2152315 B1 | 1/2016 |
| GB | 806876 A | 1/1959 |
| GB | 873526 A | 7/1961 |
| GB | 887872 A | 1/1962 |
| GB | 2165148 B | 5/1989 |
| IN | 1535DEL2004 | 8/2006 |
| JP | S61037725 A | 2/1986 |
| JP | H04056736 U | 10/1990 |
| JP | 05078634 A | 3/1993 |
| JP | 9511741 A | 11/1997 |
| JP | H09315957 A | 12/1997 |
| JP | 2001509146 A | 7/2001 |
| JP | 2001516728 A | 10/2001 |
| JP | 2002528403 A | 9/2002 |
| JP | 2002537221 A | 11/2002 |
| JP | 2003063954 A | 3/2003 |
| JP | 2003514006 A | 4/2003 |
| JP | 2004510807 A | 4/2004 |
| JP | 2004511431 A | 4/2004 |
| JP | 2009510116 A | 3/2009 |
| JP | 2010506965 A | 3/2010 |
| JP | 2010519218 A | 6/2010 |
| JP | 5286850 B2 | 9/2013 |
| WO | 9323019 A1 | 11/1993 |
| WO | 1995027481 A1 | 10/1995 |
| WO | 9621427 A1 | 7/1996 |
| WO | 9639095 A1 | 12/1996 |
| WO | 9827963 A2 | 7/1998 |
| WO | 9827963 A3 | 10/1998 |
| WO | 9858695 A1 | 12/1998 |
| WO | 9913913 A2 | 3/1999 |
| WO | 9913913 A3 | 6/1999 |
| WO | 0006117 A1 | 2/2000 |
| WO | 2000024374 A1 | 5/2000 |
| WO | 2001035929 A2 | 5/2001 |
| WO | 2001035929 A3 | 12/2001 |
| WO | 0200137 A1 | 1/2002 |
| WO | 0208351 A1 | 1/2002 |
| WO | 2002038185 A2 | 5/2002 |
| WO | 2002030393 A3 | 6/2002 |
| WO | 2002067895 A2 | 9/2002 |
| WO | 2002076344 A1 | 10/2002 |
| WO | 2002038185 A3 | 1/2003 |
| WO | 2002067895 A3 | 4/2003 |
| WO | 2003041684 A2 | 5/2003 |
| WO | 2003041685 A1 | 5/2003 |
| WO | 2003041757 A2 | 5/2003 |
| WO | 2003041684 A3 | 9/2003 |
| WO | 2003041757 A3 | 9/2003 |
| WO | 2004000269 A1 | 12/2003 |
| WO | 2004000395 A1 | 12/2003 |
| WO | 2004011054 A2 | 2/2004 |
| WO | 2004011065 A1 | 2/2004 |
| WO | 2004020439 A2 | 3/2004 |
| WO | 2004011054 A3 | 4/2004 |
| WO | 2004026357 A1 | 4/2004 |
| WO | 2004032980 A1 | 4/2004 |
| WO | 2004037259 A1 | 5/2004 |
| WO | 2004043432 A2 | 5/2004 |
| WO | 2004020439 A3 | 7/2004 |
| WO | 2004043432 A3 | 7/2004 |
| WO | 2005048989 A1 | 6/2005 |
| WO | 2005070332 A1 | 8/2005 |
| WO | 2005089670 A1 | 9/2005 |
| WO | 2005115346 A2 | 12/2005 |
| WO | 2006041942 A2 | 4/2006 |
| WO | 2006063794 A1 | 6/2006 |
| WO | 2005115346 A3 | 7/2006 |
| WO | 2007011955 A2 | 1/2007 |
| WO | 2007041410 A2 | 4/2007 |
| WO | 2007041410 A3 | 7/2007 |
| WO | 2007084460 A2 | 7/2007 |
| WO | 2007084460 A3 | 11/2007 |
| WO | 2007011955 A3 | 12/2007 |
| WO | 2008045516 A1 | 4/2008 |
| WO | 2008100532 A1 | 8/2008 |
| WO | 2008124013 A1 | 10/2008 |
| WO | 2008153611 A2 | 12/2008 |
| WO | 2006041942 A3 | 4/2009 |
| WO | 2008153611 A3 | 7/2009 |
| WO | 2009100222 A1 | 8/2009 |
| WO | 2011151355 A1 | 12/2011 |
| WO | 2011151356 A2 | 12/2011 |
| WO | 2011151356 A3 | 3/2012 |
| WO | 2012074883 A1 | 6/2012 |
| WO | 2014081343 A2 | 5/2014 |
| WO | 2014081343 A3 | 8/2014 |
| WO | 2014164754 A1 | 10/2014 |

OTHER PUBLICATIONS

Karatas, A. et al., "Studies of Release of Ketorolac Tromethamin and Indomethacin from Opthalmic Hydrogel Inserts", Ankara Ecz Fak Derg., 35(4):255-268 (2006).

Kaul, S. et al, "Polymeric-based perivascular delivery of a nitric oxide donor inhibits intimal thickening after balloon denudation arterial injury: role of nuclear factor kappaB", J Am Coli Cardio, 35(2):493-501 (Feb. 2000).

Kelava, T. et al, "Biological Actions of Drug Solvents", Periodicum Biologorum, 113(3):311-320 (2011).

Kissel, T., "ABA-triblock copolymers from biodegradable polyester A-blocks and hydrophilic poly(ethylene oxide) B-blocks as a can-

(56) References Cited

OTHER PUBLICATIONS didate for in situ forming hydrogel delivery systems for proteins," Adv Drug Deliv Rev., 54(1):99-134 (Jan. 2002).
Kranz, H. et al, "Myotoxicity studies of injectable biodegradable in-situ forming drug delivery systems", Int J Pharm., 212(1):11-18 (Jan. 5, 2001).
Kulkarni RK et al, "Polylactic acid for surgical implants", Arch Surg., 93:839-843 (1966).
Lactel Absorbable Polymers, "Inherent Viscosity vs. Molecular Weight", Durect Corporation.
Laffont, C. et al., "Population pharmacokinetics and prediction of dopamine D2 Receptor occupancy after multiple doses of RBP-700, a new sustained-release formulation of risperidone, in schizophrenia patients on stable oral risperidone treatment", Clin. Pharmacokinetics, 53:533-543 (2014).
Laffont, C.M. et al, "Population Pharmacokinetic Modeling After Repeated Administrations of RBP-6000, a New, Subcutaneously Injectable, Long-Acting, Sustained-Release Formulation of Buprenorphine, for the Treatment of Opioid Use Disorder", J Clin Pharmacol, 56(7):806-815 (Jul. 2016, e-published Mar. 11, 2016).
Lambert et al, "Development of an in situ forming biodegradable poly-lactide-co-glycolide sysytem for the controlled release of proteins", Journal of Controlled Release, 33:189-195 (1995).
Lee, K.P. et al, "Toxicity of N-methyl-2-pyrrolidone (NMP): teratogenic, subchronic, and two-year inhalation studies", Fundam Appl Toxicol., 9(2):222-235 (Aug. 1987).
Lin, X. et al, "A novel risperidone-loaded SAIB-PLGA mixture matrix depot with a reduced burst release: effects of solvents and PLGA on drug release behaviors in vitro/in vivo", J Mater Sci Mater Med., 23(2):443-455 (2012).
Li, M. et al., "A novel, non-prostanoid EP2 receptor-selective prostaglandin E2 agonist stimulates local bone formation and enhances fracture healing", Bone Miner Res., 18(11):2033-2042 (Nov. 2003).
Lu et al., "In vivo evaluation of risperidone-SAIB in situ system as a sustained release delivery system in rats", Eur. J. Pharma and Biopharma., 68:422-429 (2008).
Lu et al., "Sucrose Acetate Isobutyrate as an in situ forming system for sustained riperidone release", J. Pharm Sci., 96(12):3252-3262 (2007).
Lynch, G.S. et al, "Emerging drugs for sarcopenia: age-related muscle wasting", Expert Opin Emerg Drugs., 9(2):345-361 (Nov. 2004).
Madhu, M. et al, "Biodegradeable Injectable Implant Systems for Sustained Delivery Using Poly (Lactide-Co-Glycolide) Copolymers", International Journal of Pharmacy and Pharmaceutical Sciences, 1(1):103-107 (Nov.-Dec. 2009).
Makadia, H.K. et al, "Poly Lactic-coGlycolic Acid (PLGA) as Biodegradable Controlled Drug Delivery Carrier," Polymers, 3(3):1377-1397 (Sep. 1, 2011, e-published Aug. 26, 2011).
Malik, K. et al, "Atrigel: A Potential Parenteral Controlled Drug Delivery System," Der Pharmacia Sinica ,1(1):74-81 (2010).
Matschke, C. et al, "Sustained-release injectables formed in situ and their potential use for veterinary products", J Control Release, 85(1-3):1-15 (Dec. 2007).
McLeod, D.C. et al, "Hormonal therapy: historical perspective to future directions", Urology, 61(Suppl2A):3-7 (Feb. 2003).
Mealy (2004). "Treatment of Metabolic Disorders by Condition", Annual Update 2003/2004, Drugs of the Future, 29(8):843-872.
Medicott, N.J. et al., "Sustained release veterinary parenteral products", Adv Drug Deliv Rev, 56(10):1345-1365 (Jun. 23, 2004).
Mendelson, J.E. et al, "Lack of effect of sublingual salvinorin A, a naturally occurring kappa opioid, in humans: a placebo-controlled trial", Psychopharmacology, 214(4):933-939 (Apr. 2011, e-published Dec. 8, 2010).
Mexican Application Serial No. MX/a/2009/012781, Office Action dated Nov. 21, 2012.
Mexican Application Serial No. MX/a/2009/012781, Office Action dated Mar. 5, 2014, 4 pages.
Mexican Application Serial No. MX/a/2009/012781, Office Action dated Jun. 24, 2013—English translation, 7 pages.
Mexican Application Serial No. MX/a/2009/012781, Response filed Nov. 4, 2013 to Office Action dated Jun. 24, 2013, 17 pages.
Mexican Application Serial No. MX/a/2009/012781, Response filed Feb. 28, 2013 to Office Action dated Nov. 21, 2012, 15 pages.
Mexican Application Serial No. MX/a/2009/012781, Voluntary Amendment filed, 11 pages.
Middleton et al, "Synthetic Biodegradable Polymers as Medical devices", MDDI Medical Device and Diagnostic Industry News Products and Suppliers, 9 pages (1998).
Middleton, JC et al., "The effect of PEG end groups on the degradation of a 75/25 poly(DL-lactide-co-glycolide)", Society for Biomaterials (1999).
Miller, R.A. et al, "Degradation rates of oral resorbable implants (polylactates and polyglycolates): rate modification with changes in PLA/PGA copolymer ratios", Biomed Mater Res, 11(5):711-719 (Sep. 1977).
Mottu, F. et al, "In vitro assessment of new embolic liquids prepared from preformed polymers and water-miscible solvents for aneurysm treatment", Biomaterials, 21(8):803-811 (Apr. 2000).
Mownika, G. et al, "Formulation and Evaluation of Simvastatin Injectable in situ Implants", American Journal of Drug Discovery and Development, 2(2):87-100 (2012).
Nahata, T. et al., "Formulation optimization of long-acting depot injection of aripiprazole by using D-optimal mixture design", PDA J Pharm Sci Technol., 63(2):113-122 (Mar.-Apr. 2009).
New Zealand Application Serial No. 581862, Office Action dated Oct. 19, 2010, 3 pages.
New Zealand Application Serial No. 581862, Office Action dated Feb. 9, 2012, 2 pages.
New Zealand Application Serial No. 581862, Response filed Jan. 18, 2012 to Office Action dated Oct. 19, 2010, 30 pages.
New Zealand Application Serial No. 581862, Response filed May 10, 2012 to Office Action dated Feb. 9, 2012, 12 pages.
New Zealand Application Serial No. 597621, Office Action dated Jan. 20, 2012, 3 pages.
New Zealand Application Serial No. 597621, Office Action dated May 16, 2013, 2 pages.
New Zealand Application Serial No. 597621, Response filed Jun. 7, 2013 to Office Action dated May 16, 2013, 7 pages.
New Zealand Application Serial No. 597621, Response filed Apr. 30, 2013 to Office Action dated Jan. 20, 2012, 11 pages.
New Zealand Application Serial No. 611649, Office Action dated Feb. 5, 2014, 2 pages.
New Zealand Application Serial No. 611649, Office Action dated Apr. 7, 2014, 1 page.
New Zealand Application Serial No. 611649, Response filed Jan. 16, 2014 to Office Action dated Jun. 11, 2013, 4 pages.
New Zealand Application Serial No. 611649, Office Action dated Jun. 11, 2013, 3 pages.
Duysen, E.G. et al (1992). "Bioactivity of Polypeptide Growth Factors Released from the Atrigel Drug Delivery System", PHREEB, Abstract No. 2028.
Duysen, E.G. et al (1993). "Release of Bioactive Growth Factors from the Atrigel Delivery System in Tibial Defect and Dermal Wound Models", PHREEB, 10(10):S83, Abstract No. 2043.
Duysen, E.G. et al (1994). "An Injectable, Biodegradable Delivery System for Antineoplastic Agents", PHREEB, 11(10):S88, Abstract No. 2071.
Eliaz et al., "Characterization of a polymeric PLGA-injectable implant delivery system for the controlled release of proteins", J. Biomed. Mater. Res., 50:388-396 (2000).
Eliaz, R.E. et al, "Delivery of soluble tumor necrosis factor receptor from in-situ forming PLGA implants: in-vivo", Pharm Research, 17(12):1546-1550 (Dec. 2000).
Erickson, NM et al., "An in vitro degradation study comparing poly(DL-lactide co-glycolide) with acid end groups and ester end groups", 20th Southern Biomedical Engineering Conference (2001).
European Application Serial No. 08725543.6 Office Action dated Mar. 31, 2010, 5 pages.
European Application Serial No. 08725543.6, Communication noting Loss of rights pursuant to Rule 112(1) dated Nov. 17, 2010, 2 pages.

(56) References Cited

OTHER PUBLICATIONS

European Application Serial No. 08725543.6, Office Action dated Feb. 6, 2013, 10 pages.
European Application Serial No. 08725543.6, Response filed Jul. 11, 2013 to Office Action dated Feb. 6, 2013, 20 pages.
European Application Serial No. 08725543.6, response to filed Jan. 17, 2011 to Noting Loss of Rights dated Nov. 17, 2010 to Office action dated Mar. 31, 2010, 16 pages.
European Application Serial No. 08725543.6, Summons to Attend Oral Proceedings dated Jun. 13, 2014, 7 pages.
European Patent Application No. 08725543.6, Notice of Opposition dated Oct. 20, 2016, 5 pages.
European Patent No. 2152315, Opposition dated Oct. 6, 2016, 12 pages.
European Patent No. 2152315, Preliminary Opinion by the Opposition Division dated Sep. 8, 2017, 18 pages.
European Patent No. 2361609, Communication of a Notice of Opposition, Notice of Opposition, and Opponent's Grounds of Opposition dated May 7, 2014.
European Patent No. 2361609, Opponent written submissions dated Sep. 10, 2015, 6 pages.
European Patent No. 2361609, Opponent's Further Submission dated Mar. 6, 2017, 14 pages.
European Patent No. 2361609, Opponent's Grounds of Appeal dated Mar. 29, 2016, 13 pages.
European Patent No. 2361609, Opposition Minutes and Opinion dated Nov. 27, 2015, 20 pages.
European Patent No. 2361609, Patent owner's experimental report dated Aug. 18, 2015.
European Patent No. 2361609, Patent Owner's Response to Grounds of Appeal dated Aug. 12, 2016, 53 pages.
European Patent No. 2361609, Patent owner's written submissions dated Nov. 19, 2014, pp. 1-9.
European Patent No. 2361609, Summons to Oral Proceedings dated Feb. 16, 2015, 6 pages.
Evans, H.C., et al, "Leuprorelin: Subcutaneous Depot Formulation (Eligard) for Advanced Prostate Cancer", Am J. Cancer, 3(3)197-201 (2004).
Extracts from European Pharmacopoeia, 5th Ed., Jun. 15, 2004, pp. 5-7 & 2374-2376.
FDA Document K982865 (1998). Atrix Laboratories, Inc. 13 pages.
FDA Document K994137 (2000). Atrix Laboratories, Inc. 9 pages.
Fleischhacker et al, "Treatment of schizophrenia with long acting injectable risperidone: a 12-month open-label trail of the first acting second-generation antipsychotic", J. Clin. Psychiatry, 64(10):1250-1257 (2003).
Frank, K.R. et al, "Controlled Release of Bioactive Growth Factors from a Biodegradable Deliver System", PHREEB, 11(10):S88, Abstract No. 2070 (1994).
Furuishi, T. et al, "Effect of permeation enhancers on the in vitro percutaneous absorption of pentazocine", Biol Pharm Bull., 30(7):1350-1353 (Jul. 2007).
Gerentes, P. et al. (2002). "Study of a chitin-based gel as injectable material in periodontal surgery," Biomaterials 23(5):1295-1302.
Gharabawi et al, "Maintenance therapy with once-monthly administration of long-acting injectable riseridone in patients with schizophrenia or schizoaffective disorder: a pilot study of an extended dosing interval", Annals of General Psychiatry, 6(3):1 to 10 (Jan. 2007).
Gomeni, R. et al., "A model-based approach to characterize the population pharmacokinetics and the relationship between the pharmacokinetic and safety profiles of RBP-7000, a new, long-acting, sustained-release formulation of Risperidone", J. Clin. Pharmaco., 58(10):1010-1019 (2013).
Gou, M. et al, "Polymeric matrix for drug delivery: honokiol-loaded PCL-PEGPCL nanoparticles in PEG-PCL-PEG thermosensitive hydrogel", J Biomed Mater Res A, 93(1):219-226 (Apr. 2010).
Griffeth, R.J. et al. (2002). "Is Lucteal Production of PGF2a Required for Luteolysis?" Biology of Reproduction 66 (Supplement 1), Abstract 465, 2 pages.
Hatefi et al., "Biodegradable injectable in situ forming drug delivery system", J. of Contr. Rel., 80:9-28 (2002).
Hempel, G. et al, "Cytotoxicity of dimethylacetamide and pharmacokinetics in children receiving intravenous busulfan", J Clin Oncol, 25(13):1772-1778 (May 1, 2007).
Huang et al, "Pharmacokinetics of the novel antipsychotic agent risperidone and the prolactin response in healthy subjects", Clinical Pharmacology & Therapeutics, 54(3):257-268 (1993).
Ibrahim, H.M. et al, "Development of meloxicam in situ implant formulation by quality by design principle": Drug Dev Ind Pharm, 40(1):66-73 (Jan. 2014, e-published Jan. 9, 2013).
International Application No. PCT/US2008/001928, International Search Report and Written Opinion dated Jun. 10, 2009, 14 pages.
International Application Serial No. PCT/US2008/001928International Preliminary Report on Patentability dated Dec. 10, 2009, 11 pages.
Jain, R.A., "The manufacturing techniques of various drug loaded biodegradable poly(lactide-co-glycolide) (PLGA) devices," Biomaterials, 21(23) :2475-2490 (Dec. 2000).
Jaiswal, J. et al, "Transdermal delivery of naloxone: ex vivo permeation studies", Int J Pharm, 179(1):129-134 (Mar. 1, 1999).
Japanese Application Serial No. 2010-509326, Office Action dated Jan. 22, 2013, 10 pages.
Japanese Application Serial No. 2010-509326, Office Action dated May 14, 2013—English translation, 4 pages.
Japanese Application Serial No. 2010-509326, Response filed Apr. 18, 2013 to Office Action dated Jan. 22, 2013, 21 pages.
Jarr, E.M. et al. (Jul. 1999). "Sustained Release of Lidocaine from an Injectable Implant System for Treatment of Post-Operative," Proceedings Int'l Symp Control Rel Bioact Materials, Abstract 5423, 4 pages.
Johnson CA et al., "Biodegradable delivery systems for Estradiol: Comparison between Poly (DL-lactide) microspheres and the Saber delivery system", Proceed Int'l Symp. Control. Rel. Bioact. Mater., Controlled Release Society, Inc., 26 (1999).
Johnson, O.L.. et al. "The stabilization and encapsulation of human growth hormone into biodegradable microspheres", Pharm res., 14(6):730-735 (Jun. 1997).
New Zealand Application Serial No. 611649, Response filed Mar. 21, 2014 to Office dated Feb. 5, 2014, 2 pages.
Nyberg, S. et al, "Suggested minimal effective dose of risperidone based on PET-measured D2 and 5-HT2A receptor occupancy in schizophrenic patients", Am J Psychiatry, 156(6):869-875 (Jun. 1999).
Okumu FW et al., "Evaluation of Saber TM as a local delivery system for rhVEGF-formulation design and in vitro assessment" (2000).
Okumu FW et al., "Evaluation of the Saber TM delivery system for sustained release of growth hormone formulation design and in vivo assessment" (2001).
Okumu FW et al., "Sustained delivery of human growth hormone from a novel gel system: Saber TM", Biomaterials 23:4353-4358 (2002).
Olby, N., "The pathogenesis and treatment of acute spinal cord injuries in dogs", Vet Clin North Am Small Anim Pract, 40(5):791-807 (Sep. 2010).
Omidfar, K. et al, "Stabilization of Penicillinase-Hapten Conjugate for Enzyme Immunoassay", Journal of Immunoassay & Immunochemistry, 23(3):385-398 (2002).
Packhaeuser, C.B. et al, "In situ forming parenteral drug delivery systems: an overview," Eur J Pharm Biopharm, 58(2):445-455 (Sep. 2004).
Panaccione, C. et al, "Use of a Trinomial Distribution Probability Model in Development of a Tier-Testing Scheme for Content Uniformity Testing", Drug Information Journal, 31:903-90 (1997).
Paralkar, V.M. et al, "An EP2 receptorselective prostaglandin E2 agonist induces bone healing", PNAS USA, 100 (11):6736-6740 (May 27, 2003, e-published May 14, 2003).
Parent, M. et al, "PI-GA in situ implants formed by phase inversion: critical physicochemical parameters to modulate drug release", J Control Release, 172(1):292-304 (Nov. 28, 2013, e-published Sep. I, 2013).

(56) References Cited

OTHER PUBLICATIONS

Patel, R.B. et al., "Effect of injection site on in situ implant formation and drug release in vivo", J Control Release, 147(3):350-358 (Nov. 1, 2010, e-published Aug. 20, 2010).
Pechenov, S. et al, "Injectable controlled release formulations incorporating protein crystals", J Control Release, 96(1):149-158 (Apr. 16, 2004).
Penco M. et al., "A new chain extension reaction on poly(lactic-glycolic acid) (PLGA) thermal oligomers leading to high molecular weight PLGA-based polymeric products", Polymer International, 46:203-216 (1998).
Perez-Marreno, R., "A six-month, open-label study assessing a new formulation of leuprolide 7.5 mg for suppression of testosterone in patients with prostate cancer", Clinical Therapeutics, 24(11):1902-1914 (Nov. 2002).
Perez-Marrero, R. et al., "A subcutaneous delivery system for the extended release of leuprolide acetate for the treatment of prostate cancer", Expert Opin Pharmacother., 5(2):447-457 (Feb. 2004).
Persersis (Risperdone). Prescribing Information Insert. 42 pages (2018).
Plourde, F. et al, "First report on the efficacy of l-alanine-based in situ-forming implants for the long-term parenteral delivery of drugs", J Control Release, 108(2-3):433-441 (Nov. 28, 2005, e-published Sep. 21, 2005).
Pluta, J. et al, "In vitro studies of the properties of thermosensitive systems prepared on Pluronic F-127 as vehicles for methotrexate for delivery to solid tumours", Polymers in Medicine, 36(3):37-52 (Dec. 20, 2006).
QLT Inc/BC, "Form 10-K—Annual Report pursuant to Section 13 and 15(d)", 436 pages (2007).
Rackur, H. et al, "In-Situ Forming Implants of PLGA/Leuprolide Acetate Solutions in NMP and Their in Vitro/In Vivo Release Characteristics", 28th International Symposium on Controlled Release of Bioactive Materials and Fourth Consumer Products Conference, 2001 Proceedings, Abstract 6137, pp. 884-885 (2001).
Radomsky, M.L. et al, "The Controlled Release of Ganirelix from the Atrigel TM Injectable Implant System", Proceed Intern Symp Control Rel Bioact Mater., 20:458-459 (1993).
Rafienia, M. et al, "In Vitro Evaluation of Drug Solubility and Gamma Irradiation on the Release of Betamethasone under Simulated In Vivo Conditions", Journal of Bioactive and Compatible Polymers, 22:443-459 (Jul. 2007).
Rathbone, M.J. et al., "Modified release drug delivery in veterinary medicine," Drug Discov Today, 7(15):823-829 (Aug. 1, 2002).
Ravivarapu, H.B. et al, "Sustained activity and release of leuprolide acetate from an in situ forming polymeric implant," AAPS PharmSciTech,1(1):E1 (Feb. 28, 2000).
Ravivarapu, H.B. et al., "Parameters affecting the efficacy of a sustained release polymeric implant of leuprolide", Int J Pharm., 194(2):181-191 (Jan. 25, 2000).
Ravivarapu, H.B. et al., "Sustained suppression of pituitary-gonadal axis with an injectable, in-situ forming implant of leuprolide acetate", J Pharm Sci, 89(6):732-741 (Jun. 2000).
Reilley, K.J. et al, "Prevention of Cocaine-Conditioned Place Preference with Salvinorin a Prepared with Optimal Vehicle Conditions," 40th Annual Meeting Neuroscience 2010, Presentation Abstract, 2 pages (Nov. 17, 2010).
Risperdal Consta Data Sheet, 2003 FDA Approved, 53 pages.
Rowland et al, Clinical Pharmacokinetics Concepts and Applications (1995).
Samadi et al, "The effect of lauryl capping group on protein release and degradation of poly(D,L-lactic-co-glycolic acid) particles", Journal of Controlled Release, 172:436-443 (2013).
Schoenhammer, K. et al, "Injectable in situ forming depot systems: PEG-DAE as novel solvent for improved PLGA storage stability", Int J. Pharm., 371(1-2):33-39 (Apr. 17, 2009, e-published Dec. 24, 2008).
Schoenhammer, K. et al. (Dec. 2009, e-published Oct. I, 2009). "Poly(ethyleneglycol) 500 dimethylether as novel solvent for injectable in situ forming depots," Pharm Res, 26(12):2568-2577.

Schulman, C.C., "LHRH Agonists in Prostate Cancer Optimising Testosterone Control with Eligard", European Urology Supplements, 4:1-3 (2005).
Schwach-Abdellaoui, K. et al, "Local delivery of antimicrobial agents for the treatment of periodontal diseases", Eur J Pharm Biopharm., 50(1):83-99 (Jul. 2000).
Shakeel, F. et al., "Solubility of antipsychotic drug risperidone in Transcutol + water co-solvent mixtures at 298.15 to 333.15K", J. of Molec. Liq., 191:68-72 (2014).
Sherman, J.M. et al, "Localized Delivery of Bupivacaine HCL from Astrigel TM Formulations for the Management of Postoperative Pain", Pharmaceutical Research, 11(10), PDD7574, 2 pages (1994).
Sigma-Aldrich website, "Amtriptyline hydrochloride", p. 1-4.
Sinha & Trehan, "Biodegradable Microspheres for Parenteral Delivery", Critical Reviews in Therapeutic Drug Carrier Systems, 22(6):535-602 (2005).
Sinha, V.R. et al, "Poly-epsilon-caprolactone microspheres and nanospheres: an overview", Int J. Pharm., 278(1):1-23 (Jun. 18, 2004).
Smith DA & Tipton AJ, "A novel parenteral delivery system", AAPS-Presentation TDD 7270 Annual Meeting, Seattle, WA (1996).
Smith, R.W. et al, "A Study of Water Diffusion, in Both Radial and Axial Directions, into Biodegradable Monolithic Depots Using Ion Beam Analysis," Polymer, 45:4893-4908 (2004).
Southard, G.L. et al, "Subgingival controlled release of antimicrobial agents in the treatment of periodontal disease", Int J Antimicrob Agents, 9(4):239-253 (Feb. 1998).
Southard, G.L. et al, "The drug delivery and biomaterial attributes of the Atrigel technology in the treatment of periodontal disease", Expert Opin Investig Drugs, 7(9):1483-1491 (Sep. 1998).
Stroup, T.S. et al, "Effectiveness of Olanzapine, Quetiapine, Risperidone, and Ziprasidone in Patients with Chronic Schizophrenia Following Discontinuation of a Previous Atypical Antipsychotic", Am. J. Psychiatry, 163(4):611-622 (Apr. 2006).
Sullivan SA et al., "Incorporation of polymer microparticles into sucrose acetate isobutyrate reduces burst and extends release", Proceed Int'l Symp. Control. Rel. Bioact. Mater., Controlled Release Society, Inc., 27 (2000).
Sullivan SA et al., "Sustained release of lysozyme from the Saber delivery system", AAPS, New Orleans, LA (1999).
Sullivan SA et al., "Sustained release of lysozyme from the Saber delivery system", Poster, Southern Biosystems, Inc., Birmingham, AL, AAPS, New Orleans, LA (1999).
Sullivan SA et al., "Sustained release of orally administered active using Saber TM delivery system incorporated into soft gelatin capsules", Proceed Int'l Symp. Control Rel. Bioact. Mater., Controlled Release Society, Inc., 25 (1998).
Sundaram, S. et al, "Peptides: Nasal and Pulmonary Delivery of Deslorelin, a Peptide Drug," American Pharmaceutical Review, 130-139 (2004).
Swanson, B.N., "Medical use of dimethyl sulfoxide (DMSO)", Rev Clin Basic Pharm., 5(1-2):1-33 (Jan.-Jun. 1985).
Tipton, A.J. et al, "A Biodegradable, Injectable Delivery System for Non-Steroidal Anti-Flammatory Drugs," Pharmaceutical Research, 8(10), PDD 7279, 2 pages (Oct. 1991).
Toot, J.D. et al, "P124—Drug Discrimination Testing & Substitution Assess ments in Adult Male SD Rats of Morphine Prepared in Multiple Vehicle" and "P125—Self-Administration Assessment and Bioanalytical Analysis of Morphine in Adult Male Rats", International Journal of Toxicology, 32(1):66 (2013).
Tserki, V. et al,"Biodegradable aliphatic polyesters. Part II. Synthesis and characterization of chain extended poly (butylene succinate-co-butylene adipate)", Polymer Degradation and Stability, 91(2):377-384 (Feb. 2006).
Tunn, U.W. "A 6-month depot formulation of leuprolide acetate is safe and effective in daily clinical practice: a non-interventional prospective study in 1273 patients", BMC Urology, 11:15 (Jul. 29, 2011).
U.S. Appl. No. 14/490,082, Office Action dated Oct. 10, 2014, 12 pages.

(56) References Cited

OTHER PUBLICATIONS

Wang et al., "Synthesis, characterization, biodegration, and drug delivery application of biodegradable lactic/glycolic acid polymers: I. Synthesis and characterization", J. Biomater. Sci. Polymer Edn, 11(3):301-318 (2000).
Wang, L. et al, "Structure formation in injectable poly(lactide-coglycolide) depots", J Control Release, 90(3):345-354 (Jul. 31, 2003).
Wang, L. et al, "Design of a long-term antipsychotic in situ forming implant and its release control method and mechanism," Int J Pharm, 427(2):284-292 (May 10, 2012, e-published Feb. 23, 2012).
Wang, L. et al. "Drug release from injectable depots: two different in vitro mechanisms", J Control Release, 99(2):207-216 (Sep. 30, 2004).
Wikipedia. 2016. "Risperidone", (Accesssed on Oct. 10, 2016), 8 pages [Retrieved from: https://en.wikipedia.org/w/indez.php?title=Risperidone&printable=yes>].
Wikipedia. 2019. "Ethyl Benzoate" (Accessed on Mar. 29, 2019) 3 pages [Retrieved from: https://en.wikipedia.org/wiki/Ethyl_benzoate].
Wikipedia. 2019. "Triacetin" (Accessed on Mar. 29, 2019) 5 pages [Retireved from: https://en.wikipedia.org/Triacetin].
Winzenburg, G. et al, "Biodegradable polymers and their potential use in parenteral veterinary drug delivery systems," Adv Drug Deliv Rev., 56(10):1453-1466 (Jun. 23, 2004).
Wischke, C. et al, "Development of PLGA-based injectable delivery systems for hydrophobic fenretinide", Pharm Res, 27(10):2063-2074 (Oct. 2010, e-published Jul. 29, 2010).
Wolff, E.D. et al. (1994). "Use of Bio-Beads SM-4 Adsorbent for Bioburden Testing of Atrigel TM Biodegradable Delivery System Containing 10% Doxycycline," ASM Las Vegas 1994, Abstracts, 3 pages.
World Health Organization (2001). N-Methyl-2-Pyrrolidone, Concise International Chemical Assessment Document 35, 39 pages.
Wright, J., "Experimental Report—In Vitro Release Profiles for Formulations containing Amitripyline hydrochloride", submitted in European Patent No. 2 361 609 (Aug. 10, 2016).
PCT Application No. PCT/US2014/023397, Written Opinion dated Sep. 15, 2015.
Wu, Z. et al, "Thermosensitive hydrogel used in dual drug delivery system with paclitaxel-loaded micelles for in situ treatment of lung cancer", Colloids Surf B Biointerfaces, 122:90-98 (Oct. 2014, e-published Jul. 1, 2014).
Xia, Y. et al., "Uniform biodegradable microparticle systems for controlled release", J Control Release, 82(1):137-147 (Jul. 18, 2002).
Yaksh, T.L. et al,"The utility of 2-hydroxypropyl-beta-cyclodextrin as a vehicle for the intracerebral and intrathecal administration of drugs", Life Sci, 48(7):623-633 (1991).
Yang, Y. et al, "Improved initial burst of estradiol organogel as long-term in situ drug delivery implant: formulation, in vitro and in vivo characterization", Drug Dev Ind Pharm., 38(5):550-556 (May 2012, e-published Mar. 15, 2012).
Yapar, E. et al., "Injectable In Situ forming microparticles: A novel drug delivery system", Tropical J. of Pharmaceut. Research, 11(2):307-318 (2012).
Yehia, S.A. et al, "A novel injectable in situ forming poly-DL-lactide and DL-lactide/glycolide implant containing lipospheres for controlled drug delivery", J Liposome Res., 22(2):128-138 (Jun. 2012, e-published Nov. 18, 2011).
Zhu, G. et al, "Stabilization of proteins encapsulated in cylindrical poly(lactide-coglycolide) implants: mechanism of stabilization by basic additives", Pharm Res., 17(3):351-357 (2000).
Ahmed, T.A. et al, "Biodegradable injectable in situ implants and microparticles for sustained release of montelukast: in vitro release, pharmacokinetics, and stability," AAPS PharmSciTech, 15(3):772-780 (Jun. 2015, e-published Mar. 20, 2014).
Ahmed, T.A. et al, "Development of biodegradable in situ implant and microparticle injectable formulations for sustained delivery of haloperidol," J Pharm Sci., 101(10):3753-3762 (Oct. 2012, e-published Jun. 29, 2012).
Aird, J., "Controlled Release-SMi Conference, Meeting Report Controlled Release, London,UK," IDrugs, 6(4):334-336 (2003).
Anonymous: "Form 10-K QLT Inc." Mar. 1, 2007. 137 pages (Accessed on May 14, 2009) Retrieved from: http://www.qltinc.com/QLTinc?_downloads/investment/10k-2006.pdf>.
Anonymous: "US Securities and Exchange Commission" Mar. 1, 2007. 1 pages (Accessed on May 14, 2009) Retrieved from: http://www.sec.gov/Archives/edgar/data/827809/000094523407000108/0000945234-07-000108-index.idea.htm.
Astaneh, R. et al., "Changes in morphology of in situ forming PLGA implant prepared by different polymer molecular weight and its effect on release behavior", Journal of Pharmaceutical Sciences, 98(1):135-145 (Jan. 2009).
Australian Application Serial No. 2008262545, Examiner Report dated Oct. 15, 2012, 5 pages.
Australian Application Serial No. 2008262545, Examiner Report dated Jun. 19, 2013, 5 pages.
Australian Application Serial No. 2008262545, Response filed Nov. 13, 2013 to Examiner Report dated Jun. 19, 2013, 21 pages.
Australian Application Serial No. 2008262545, Response filed May 27, 2013 to Examiner Report dated Oct. 15, 2012, 26 pages.
Babu, R.J. et al, "Effect of penetration enhancers on the transdermal delivery of bupranolol through rat skin," Drug Deliv., 12(3):165-169 (May-Jun. 2005).
Baker, D.L. et al, "Gonadotropin-releasing hormone agonist: a new approach to reversible contraception in female deer," Journal of Wildlife Diseases, 40(4):713-724 (Oct. 2004).
Bartsch, W., et al, "Acute Toxicity in Various Solvents in the Mouse and Rat", Arzneimittel-Forschung, Drug Research, 26:1581-1583 (1976).
Basu, S.K., et al, "Protein crystals for the delivery of biopharmaceuticals," Expert Opinion Biological Therapy, 4(3)301-317 (Mar. 2004).
Becci, P.J.,. et al, "Subchronic Feeding Study in Beagle Dogs of N-Methylpyrrolidone," Journal of Applied Toxicology, 3(2):83-86 (1983).
Berge, L. et al, "Pharmaceutical Salts", J. of Pharmaceut. Sci., 66:1-19 (1977).
Berges, R., et al, "Eligard: Pharmacokinetics, Effect on Testosterone and PSA Levels and Tolerability", European Urology Supplements, 4:20-25 (2005).
Boongird, A. et al, "Biocompatibility study of glycofurol in rat brains", Exp Biol Med, 236:77-83 (Jan. 2011).
Bowersock, T.L. et al, "Vaccine delivery to animals," Adv Drug Deliv Rev., 38(2):167-194 (1999).
Brodbeck et al, "Phase inversion dynamics of PLGA solutions related to drug delivery. Part II. The role of solution thermodynamics & bath-side mass transfer", 62:333-344 (1999).
Bromberg, L.E. et al., "Sustained release of silver from periodontal wafers for treatment of periodontitis", J Control Release, 68(1):63-72 (Jul. 31, 2000).
Buggins, T.R. et al, "The effects of pharmaceutical excipients on drug disposition", Adv Drug Deliv Rev., 59(15):1482-1503 (Dec. 22, 2007).
Canadian Application Serial No. 2,687,979, Office Action dated May 7, 2014, 4 pages.
Carraway KM et al., "Drug release from a controlled release aerosol: Effect of formulation variables", Southern Biosystems, Inc., Birmingham, AL.AAPS, Indianapolis, Nov. 2000.
Chandrashekar, B.L. et al, "Sustained Release of Leuprolide Acetate from an In-situ Forming Biodegradable Polymeric Implant as the Delivery Vehicle", Proceed Int'l Symp Control Rel Bioact Mater., 26:1-3 (Jul. 1999).
Chen, F.A. et al, "Biodegradable polymer-mediated intratumoral delivery of cisplatin for treatment of human head and neck squamous cell carcinoma in a chimeric mouse model", Head Neck, 25(7):554-560 (Jul. 2003).

(56) References Cited

OTHER PUBLICATIONS

Cheng, Y. et al, "Thermosensitive hydrogels based on polypeptides for localized and sustained delivery of anticancer drugs," Biomaterials, 34(38):10338-10347 (Dec. 2013, e-published Oct. 1, 2013).
Chinese Application Serial No. 200880100394.0, Decision on Rejection dated Sep. 3, 2013—English translation, 11 pages.
Chinese Application Serial No. 200880100394.0, Office Action dated Apr. 2, 2013, 10 pages.
Chinese Application Serial No. 200880100394.0, Office Action dated Jul. 25, 2012, 25 pages.
Chinese Application Serial No. 200880100394.0, Request for Reexamination filed Dec. 18, 2013 in Response to Decision on Rejection dated Sep. 3, 2013—English translation, 11 pages.
Chinese Application Serial No. 200880100394.0, Response filed Oct. 9, 2012 to Office Action dated Jul. 25, 2012, 12 pages.
Chinese Application Serial No. 200880100394.0, Response filed Mar. 9, 2012 to Decision on Office Action dated Oct. 25, 2011, 16 pages.
Chinese Application Serial No. 200880100394.0, Response filed Jun. 17, 2013 to Office Action dated Apr. 2, 2013—English translation, 19 pages.
Chu, F.M. et al, "A clinical study of 22.5 mg. La-2550: A new subcutaneous depot delivery system for leuprolide acetate for the treatment of prostate cancer", Journal of Urology, 168(3):1199-1203 (Sep. 2002).
Coonts, B.A. et al. (Oct. 1993). "Plasma Concentrations of Naltrexone Base Following Subcutaneous and Intramuscluar Injections of Atrigel TM Formulations in Dogs," Pharmaceutical Research: Official Journal of the American Association of Pharmaceutical Scientists PHREEB 7071 , 2 pages.
Cox, M.C. et al, "Leuprolide acetate given by a subcutaneous extended release injection: less of a pain?" Exper Rev Anticancer Ther , 5(4):605-611 (Aug. 2005).
Crawford, E.D. et al, "A 12-month clinical study of LA-2585 (45.0 mg): a new 6-month subcutaneous delivery system for leuprolide acetate for the treatment of prostate cancer", Journal of Urology, 175(2):533-536 (Feb. 2006).
Dadey, E.J. (2008). The Atrigel Drug Delivery System. In: Rathbone et al Eds, Modified-Release Drug Delivery Technology, 2nd Ed., New York, pp. 183-190.
Dernell, W.S. et al, "Apparent interaction of dimethyl sulfoxide with cisplatin released from polymer delivery devices injected subcutaneously in dogs," J Drug Target, 5(5):391-396 (1998).
Desai et al, "Surface modification of polymer biomaterials for reduced thrombogenicity", Polym. Mater. Sci. Eng., 63:731-735 (1991).
Dewan, I. et al, "Study of Release Kinetics of Dexamethasone from Biodegradable PLA In-Situ Implants", International Journal of Pharmaceutical Science and Research, 2(11):3039-3045 (2011).
Dhiman et al, "Poly(DL-lactide-co-glycolide) based delivery systems for vaccines and drugs", Indian Journal of Experimental Biology, 38:746-752 (Aug. 2000).
Domb, A.J. et al, "Solid-State and Solution Stability of Poly(anhydrides) and Polyesters", Macromolecules, 22(5)2117-2122 (1989).
Dong et al., "Development of injectable biodegradable in-situ forming gel implants", Progress in Pharmaceutical Sciences, 31:109-113 (2007).
Dunn, R.L. et al, "Sustained Release of Cisplatin in Dogs from an Injectable Implant Delivery System", Journal of Bioactive and Compatible Polymers, 11:286-300 (1996).
Dunn, R.S., (2003). "The Atrigel Drug Delivery System," Modified-Release Drug Delivery Technology, Edited by Rathbone, Hadgraft, Roberts, Marcel Dekker, Inc., Chapter 54, pp. 647-655.
"Gel", Concise Chemical and Technical Dictionary, 4th ed., Chemical Publishing Co., Inc., p. 567, New York, NY (1986).
"Relday: First once-monthly subcutaneous risperidone for the management of schizophrenia", Partnering Overview (2013).
Hou, H et al, Commonly Used Auxiliary Materials Application Technology, Edited by the National Engineering Research Center for Pharmaceutical Preparations, Department of Pharmaceutical Preparations, Shanghai Pharmaceutical Industry Research Institute, China Medical Science and Technology Press, 223-226 (2001).
Japanese Application No. 2008-533726, Office Action dated Jun. 15, 2012—English translation.
Japanese Patent Application No. 2013-002422, Office Action dated Apr. 14, 2015—English translation.
Price, M. et al, Therapeutic Drug Monitoring, 19:333-337 (1997).
Tipton, AJ., "Sucrose Acetate Isobutyrate (SAIB) for Parenteral Delivery", Reprinted from Modified-Release Drug Delivery Technology, Rathbone, Hadgraft, Roberts (Eds.) (2002).
Wikipedia. 2013. "Gel" (Accessed on Jul. 23, 2013), 5 pages [Retrieved from: https://en.wikipedia.org/wiki/Gel>].

* cited by examiner

SUSTAINED RELEASE SMALL MOLECULE DRUG FORMULATION

CROSS REFERENCE TO RELATED APPLICATIONS

This application is a continuation of U.S. application Ser. No. 16/044,259 filed Jul. 24, 2018, issued as U.S. Pat. No. 10,406,160, which is a continuation of U.S. application Ser. No. 15/422,626 filed Feb. 2, 2017, issued as U.S. Pat. No. 10,058,554, which is a continuation of U.S. application Ser. No. 14/701,173 filed Apr. 30, 2015, issued as U.S. Pat. No. 9,597,402, which is a continuation of U.S. application Ser. No. 13/790,930 filled Mar. 8, 2013, issued as U.S. Pat. No. 9,044,450, which is a continuation of U.S. application Ser. No. 11/535,398 filled Sep. 26, 2006, issued as U.S. Pat. No. 8,852,638, which claims priority to U.S. Application No. 60/722,845 filed Sep. 30, 2005; the disclosures of each of which are expressly incorporated by reference herein in their entireties.

BACKGROUND OF THE INVENTION

The invention relates generally to delivery of small molecule drugs.

The term "small molecule drug," as used herein, refers to beneficial agents having low molecular weight. The beneficial agents are usually synthesized by organic chemistry, but may also be isolated from natural sources such as plants, fungi, and microbes. The common routes for delivering small molecule drugs are oral, injection, pulmonary, and transdermal.

Many psychotherapeutic drugs are small molecule drugs and are usually provided as oral pills or bolus injections that can be administered one or more times daily. However, oral pills and bolus injections may not be optimal routes for administering small molecule psychotherapeutic drugs because of the peaks and troughs observed in plasma concentration after dosing. Adverse effects and loss of therapeutic effect have been associated with plasma concentration peaks and troughs, respectively.

From the foregoing, psychotherapy as well as other forms of therapy presently relying on small molecule drugs administered in. the form of oral pills and bolus injections may benefit from a sustained release dosage form designed to minimize variations in plasma concentration following dosing. Administration of psychotherapeutic agents as sustained release formulations will also increase patient compliance.

BRIEF SUMMARY OF THE INVENTION

In one aspect, the invention relates to an injectable depot formulation which comprises a biocompatible polymer, an organic solvent combined with the biocompatible polymer to form a viscous gel, and a small molecule drug incorporated in the viscous gel such that the formulation exhibits an in vivo release profile having $C_{max}$ to $C_{min}$ ratio less than 200 and lag time less than 0.2.

In another aspect, the invention relates to a method of administering a small molecule drug to a subject in a controlled manner which comprises implanting in the subject an effective amount of an injectable depot formulation comprising a biocompatible polymer, an organic solvent combined with the biocompatible polymer to form a viscous gel, and a small molecule drug incorporated in the viscous gel such that the formulation exhibits an in vivo release profile having $C_{max}$ to $C_{min}$ ratio less than 200 and lag time less than 0.2.

Other features and advantages of the invention will be apparent from the following description.

DETAILED DESCRIPTION OF THE INVENTION

Figure 1:
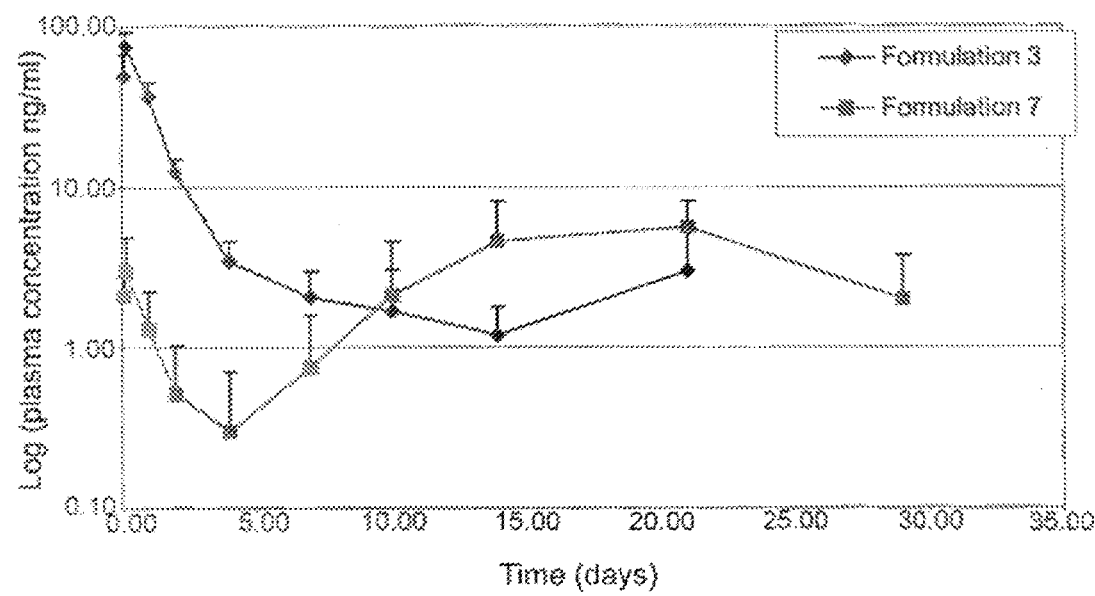
FIG. 1 shows influence of drug salt form on in vivo release profile of formulations according to embodiments of the invention.

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings and discussions that follow.

The invention is based in part on the discovery that incorporation of a sparingly soluble small molecule drug in a depot gel vehicle produces a small molecule drug formulation that has near zero-order release in vivo. The release profile shows minimal lag time and burst. For a depot formulation, this release profile is surprising because the prevailing thought in the art is that a low burst, near zero-order release is virtually impossible to attain unless special steps are taken, such as coatings for drugs and microencapsulation. Several small drug formulations have been identified in this invention with in vivo release profiles having a $C_{max}$ to $C_{min}$ ratio less than 200 and lag time, $T_{lag}$, less than 0.2.

The variable "$C_{min}$" is the minimum drug concentration in plasma or serum. The variable "$C_{max}$" is the maximum drug concentration in plasma or serum. The variable "$T_{lag}$" is the ratio of $T_{valley}$ to $T_{total}$, where $T_{valley}$ is less than $T_{total}$. The variable "$T_{valley}$" is the time to reach $C_{valley}$. The variable "$C_{valley}$" is the first trough of drug concentration in plasma or serum during release. The variable "$T_{total}$" is the total release duration.

Small molecule drug formulations according to embodiments of the invention can be prepared as depot injections. The environment of use is a fluid environment and may include a subcutaneous, intramuscular, intramyocardial, adventitial, intratumoral, or intracerebral portion, a wound site, or tight joint spaces or body cavity of a human or animal. Multiple or repeated injections may be administered to the subject, for example, when the therapeutic effect of the drug has subsided or the period of time for the drug to have a therapeutic effect has lapsed or when the subject requires further administration of the drug for any reason. The formulation serves as an implanted sustained release drug delivery system after injection into the subject. Such controlled release can be over a period of one week, more than one week, one month, or more than one month. Preferably, the controlled release is over at least a period of one week, more preferably over a period of at least one month.

A small molecule drug formulation according to an embodiment of the invention includes a depot gel vehicle. The depot gel vehicle includes a biocompatible polymer, i.e., a polymer that would not cause irritation or necrosis in the environment of use. Biocompatible polymers that may be useful in the invention may be bioerodible, i.e., gradually decompose, dissolve, hydrolyze and/or erode in situ. Examples of bioerodible polymers include, but are not limited to, polylactides, polyglycolides, polycaprolactones, polyanhydrides, polyamines, polyurethanes, polyester-amides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, terpolymers and mixtures thereof. The polymer is typically present in the depot gel vehicle in an amount ranging from about 5 to 80% by weight, preferably from about 20 to 70%, often from about 40 to 60% by weight.

In one embodiment, the polymer is a polylactide. A polylactide polymer is a polymer based on lactic acid or a copolymer based on lactic acid and glycolic acid. The polylactide polymer can include small amounts of other comonomers that do not substantially affect the advantageous results that can be achieved in accordance with the invention. The term "lactic acid" includes the isomers L-lactic acid, D-lactic acid, DL-lactic acid, and lactide. The term "glycolic acid" includes glycolide. The polymer may have a lactic-acid to glycolic-acid monomer ratio of from about 100:0 to 15:85, preferably from about 60:40 to 75:25, often about 50:50. The polylactide polymer has a number average molecular weight ranging from about 1,000 to about 120,000, preferably from about 5,000 to about 30,000, as determined by gel permeation chromatography. Suitable polylactide polymers are available commercially.

The depot gel vehicle further includes a biocompatible solvent which when combined with the polymer forms a viscous gel, typically exhibiting viscosity in a range from 500 poise to 200,000 poise, preferably from about 1,000 poise to 50,000 poise. The solvent used in the depot gel vehicle is typically an organic solvent and may be a single solvent or a mixture of solvents. To limit water intake by the depot gel vehicle in the environment of use, the solvent, or at least one of the components of the solvent in the case of a multi-component solvent, preferably has limited miscibility with water, e.g., less than 7% by weight, preferably less than 5% by weight, more preferably less than 3% by weight miscibility with water. Examples of suitable solvents include, but are not limited to, benzyl benzoate (BB), benzyl alcohol (BA), ethyl benzoate (EB), triacetin, and N-methyl-2-pyrrolidone (NMP). The solvent is typically present in the depot gel vehicle in an amount ranging from about 20 to 95% by weight, preferably in an amount ranging from about 30 to 80% by weight, often in an amount ranging from about 40 to 60% by weight.

A formulation according to an embodiment of the invention includes a small molecule drug dispersed or dissolved in a depot gel vehicle as described above. The term "dispersed or dissolved" is intended to encompass all means of establishing the presence of the small molecule drug in the viscous gel and includes dissolution, dispersion, suspension, and the like. Small molecule drugs used in formulations of the invention are sparingly soluble in water. In a preferred embodiment, small molecule drugs used in formulations of the invention have less than 1 mg/ml solubility in water. In one embodiment, small molecule drugs used in formulations of the invention have a molecular weight in a range from 200 to 2,000 Daltons. Small molecule drugs used in formulations of the invention may have a narrow or wide therapeutic window. However, the invention generally delivers salubrious results in terms of $C_{max}$ and toxicity control for small molecule drugs having a narrow therapeutic window. The small molecule drug is typically present in the formulation in an amount ranging from about 1 to 50% by weight, more preferably in an amount ranging from about 5 to 40% by weight, often in an amount ranging from about 10 to 30% by weight.

In one embodiment, a small molecule drug formulation includes a small molecule psychotherapeutic drug, such as a small molecule antipsychotic, dopamine receptor agonist, dopamine receptor antagonist, serotonin receptor agonist, serotonin receptor antagonist, and serotonin uptake inhibitor drug. Table 1 below shows physiochemical properties of some small molecule psychotherapeutic drugs. R209130-base has the molecular formula $C_{19}H_{20}FNO$. R209130-mandelic acid salt (R209130) has the molecular formula $C_{19}H_{20}FNO \cdot C_8H_8O_3$. R209130-tartaric acid salt (R167154) has the molecular formula $C_{19}H_{20}FNO \cdot C4_HH_6O_6$. R209130 and its analogs possess putative atypical antipsychotic properties and have demonstrated antianxiety, antidepressive, and socializing effects in animal models. These characteristics may be attributed to R209130 dual antagonism of central dopamine $D_2$ receptors, serotonin $5-HT_{2A}$ and $5-HT_{2C}$ receptors, and the inhibition norepinephrine uptake. Risperidone-base has the molecular formula $C_{23}H_{27}FN_4O_2$. Risperidone-pamoate has the molecular formula $C_{23}H_{27}FN_4O_2 \cdot C_{23}H_{16}O_6$. Risperidone is a combined serotonin ($5-HT_2$) and dopamine (D2) receptor antagonist.

TABLE 1

| Property | R209130 | R167154 | R209130 base | Risperidone base | Risperidone pamoate |
|---|---|---|---|---|---|
| pKa | 9.2 | 9.2 | 9.2 | 8.2/3.1 | 8.2/3.1 |
| Solubility in H₂O (mg/ml) | 0.32 (pH 4.9) | 41.84 (pH 3.4) | 0.008 (pH 9.5) | 0.09 (pH 8.8) | 0.2 (pH 7.2) |
| Solubility at pH 7 (mg/ml) | 0.35 | 6.1 (pH 6.5) | 2 | 1 | 0.2 (pH 7.2) |
| Solubility in BB (µg/ml) | 58.6 at 40° C. | 10.3 at 40° C. | >200,000 | 32,000 | 50 |
| Solubility in BA (mg/ml) | 7.3 at 40° C. | 41.3 at 40° C. | >200,000 | 407 | 2.97 |
| Intrinsic | 0.054 | 3.7 | 0.7 | 0.0025 | N/A |

TABLE 1-continued

| Property | R209130 | R167154 | R209130 base | Risperidone base | Risperidone pamoate |
|---|---|---|---|---|---|
| dissolution rate (mg/cm$^2$.min) | | | | | |
| LogP (C$_8$OH/pH 7 buffer) | 3.9 | 4.0 | N/A | 3.04 | N/A |
| Molecular weight | 449.5 | 447.5 | 297.4 | 410.5 | 798.5 |

A study was conducted to determine the PK profile of a small molecule drug delivered from a depot gel vehicle according to the invention and the influence of salt form of the drug, solvent type, polymer type, polymer molecular weight, polymer/solvent ratio, drug loading, and particle size on the PK profile.

The following examples are presented for illustration purposes and are not intended to limit the invention as otherwise described herein.

Example 1

A depot gel vehicle was prepared as follows: A HDPE container was tared on a Mettler PJ3000 top loader balance. Poly D,L-lactide-co-glycolide (PLGA), (L/G ratio of 50/50), available as RESOMER® RG 502 (PLGA-502), was weighed into the container. The container containing PLGA-502 was tared, and the corresponding solvent was added to the PLGA-502. Amounts expressed as percentages for various combinations of PLGA-502 and solvent are set forth below in Table 2. A hybrid mixer was used to mix the PLGA-502 and solvent mixture, resulting in a clear gel-like solution of the polymer in the solvent.

TABLE 2

| Formulation | PLGA-502 (wt %, g) | Benzyl Benzoate (wt %, g) | Benzyl Alcohol (wt %, g) |
|---|---|---|---|
| A | 50.067 | 50.044 | |
| B | 50.023 | 24.988 | 24.988 |
| C | 50.365 | 45.093 | 5.1780 |
| D | 50.139 | 37.553 | 12.560 |
| E | 50.350 | 45.193 | |

Additional depot gel vehicles were prepared with solvents, selected from benzyl benzoate (BB), benzyl alcohol (BA), ethyl benzoate (EB), ethyl hydroxide (EtOH), triacetin, and N-methyl-2-pyrrolidone (NMP), and mixtures thereof, and polymers, selected from Poly D,L-lactide, available as RESOMER® L 104, RESOMER® R 104, RESOMER® 202, RESOMER® 203, RESOMER® 206, RESOMER® 207, RESOMER® 208; PLGA, L/G ratio of 50/50, available as RESOMER® RG 502H; PLGA, L/G ratio of 50/50, available as RESOMER® RG 503; PLGA, L/G ratio of 50/50, available as RESOMER® RG 755; Poly L-lactide, molecular weight of 2000, available as RESOMER® L 206, RESOMER® L 207, RESOMER® L 209, RESOMER® L 214; Poly L-lactide-co-D,L-lactide, L/G ratio of 90/10, available as RESOMER® LR 209; PLGA, L/G ratio of 75/25, available as RESOMER® RG 752, RESOMER® RG 756, PLGA, L/G ratio of 85/15, available as RESOMER® RG 858; Poly L-lactide-co-trimethylene carbonate, L/G ratio of 70/30, available as RESOMER® LT 706, and Poly dioxanone, available as RESOMER® X210 (Boehringer Ingelheim Chemicals, Inc. Petersburg, Va.); DL-lactide/glycolide (DL), L/G ratio of 100/0, available as MEDISORB® Polymer 100 DL High, MEDISORB® Polymer 100 DL Low; DL-lactide/glycolide (DL), L/G ratio of 85/15, available as MEDISORB® Polymer 8515 DL High, MEDISORB® Polymer 8515 DL Low; DL-lactide/glycolide (DL), L/G ratio of 75/25, available as MEDISORB® Polymer 7525 DL High, MEDISORB® Polymer 7525 DL Low; DL-lactide/glycolide (DL), L/G ratio of 65/35, available as MEDISORB® Polymer 6535 DL High, MEDISORB® Polymer 6535 DL Low; DL-lactide/glycolide (DL), L/G ratio of 54/46, available as MEDISORB® Polymer 5050 DL High, MEDISORB® Polymer 5050 DL Low, MEDISORB® 5050 Polymer DL 2A(3), MEDISORB® 5050 Polymer DL 3A(3), MEDISORB® 5050 Polymer DL 4A(3) (Medisorb Technologies International L.P., Cincinnati, Ohio); and PLGA (L/G ratio of 50/50), PLGA (L/G ratio of 65/35), PLGA (L/G ratio of 75/25), PLGA (L/G ratio of 85/15), Poly D,L-lactide, Poly L-lactide, Poly glycolide, Poly c-caprolactone, Poly D,L-lactide-co-caprolactone (L/C ratio of 25/75), and Poly D,L-lactide-co-caprolactone (L/C ratio of 75/25), available from Birmingham Polymers, Inc., Birmingham, Ala. Polycaprolactone-glycolic acid-lactic acid copolymer (PCL-GA-LA) was also used either mixed with polyvinylpyrrolidone (PVP) or by itself. Typical molecular weights of these polymers are in the range of 6,000 to 20,000.

Example 2

Drug particles were prepared as follows: 8209130, R167154, risperidone base, or risperidone pamoate drug was passed through sieves of different sizes to obtain drug particles having a certain range of particle size distribution. Particles in the range of 20 to 63 μm, 63 to 125 μm, 75 to 125 μm, or less than 38 μm were obtained. Micronized particles received were also used as drug particles.

Example 3

Depot formulations were prepared as follows: sieved drug particles prepared as described in Example 2 were added into the depot gel vehicles prepared as described in Example 1 in an amount of 0 to 50% by weight and blended manually until the drug particles were wetted completely. Then, the mixture of drug particles and depot gel was thoroughly blended by conventional mixing using a Caframo mechanical stirrer with an attached square-tip metal spatula. Final homogeneous gel formulations were transferred to 3, 10, or 30 cc disposable syringes for storage or dispensing.

Example 4

A representative number of implantable gels were prepared in accordance with the foregoing procedures and tested in vivo in rats to determine release of the drug as determined by blood serum or plasma concentration of drug as a function of time.

In general, in vivo studies in rats were performed following an open protocol to determine plasma levels of the drug (e.g., R209130, R167154, risperidone base, risperidone pamoate) upon systemic administration of the drug via the implant systems of the invention. Depot gel formulations containing the drug, prepared as described in the Examples above, were loaded into 0.5 cc disposable syringes. Disposable needles (18 gauge) were attached to the syringes and heated to 37° C. using a circulator bath. The depot gel formulations were injected into rats. Blood was drawn at specified time intervals and analyzed for drug content. All plasma samples were stored at 4° C. prior to analysis.

Example 5

This example investigates influence of drug salt form on in vivo release of small molecule drugs from depot gel vehicles.

Particles of R209130 and R167154, in appropriate size range, were incorporated in depot gel vehicles, as per procedure in Example 3. Resulting formulations are illustrated in Table 3 below. Final homogeneous depot formulations were transferred to 3, 10, or 30 cc disposable syringes for storage or dispensing. In vivo release of the drugs were analyzed, as per procedure in Example 4. In vivo release profiles of the formulations are shown in FIG. 1. $C_{max}$ to $C_{min}$ ratio and $T_{lag}$ of the formulations are shown in Table 2. R167154 and 8209130 are different salt forms of the same drug. Formulation 7 (R209130) has $C_{max}$ to $C_{min}$ ratio of 19.2 and $T_{lag}$ of 0.61, while formulation 3 (R167154) has $C_{max}$ to $C_{min}$ ratio of 25.7 and $T_{lag}$ of 0.33. This example shows that in vivo release is influenced by salt form of the formulation. Even though $T_{lag}$ for formulation 7 (R209130) is higher than $T_{lag}$ for formulation 3 (R167154), formulation 7 appears to have better release rate profile and duration of release in comparison to formulation 3.

TABLE 3

| No. | PLGA (Wt %) | BA (wt %) | BB (wt %) | Triacetin (Wt %) | Drug (Wt %) | $C_{max}/C_{min}$ | $T_{lag}$ |
|---|---|---|---|---|---|---|---|
| 3[2,a,II,α,A] | 45 | 22.5 | 22.5 | 0 | 10 | 25.7 | 0.33 |
| 7[1,a,II,α,B] | 45 | 22.5 | 22.5 | 0 | 10 | 19.2 | 0.61 |

[1]= R209130, [2]= R167154, [3]= risperidone base, [4]= risperidone pamoate;

TABLE 3-continued

| No. | PLGA (Wt %) | BA (wt %) | BB (wt %) | Triacetin (Wt %) | Drug (Wt %) | $C_{max}/C_{min}$ | $T_{lag}$ |
|---|---|---|---|---|---|---|---|

[a]= 50/50 PLGA-502 (MW = 16,000), [b]= 50/50 PLGA-502H (MW = 11,000), [c]= 50/50 PLGA (MW = 6400), [d]= 40/55/5 PCL-GA-LA (MW = ~13,500), [e]= 75/25 PLGA (MW = 14,300), [f]= 80/20 PCL-GA-LA/PVP, [g]= RG502:RG502H (1:1);
[α]= P/S ratio of 50/50, [β]= P/S ratio of 40/60, [γ]= P/S ratio of 45/55, [δ]= P/S ratio of 60/40, [ε]= P/S ratio of 55/45;
[A]= 63-125 μm, [B]= 20-63 μm, [C]= 75-125 μm, [D]= <38 μm, [E]= micronized, [F]= as is, [G]= not applicable;
NV = no valley

Example 6

This example investigates influence of solvent type on in vivo release of small molecule drugs from depot gel vehicles.

Figure 2:
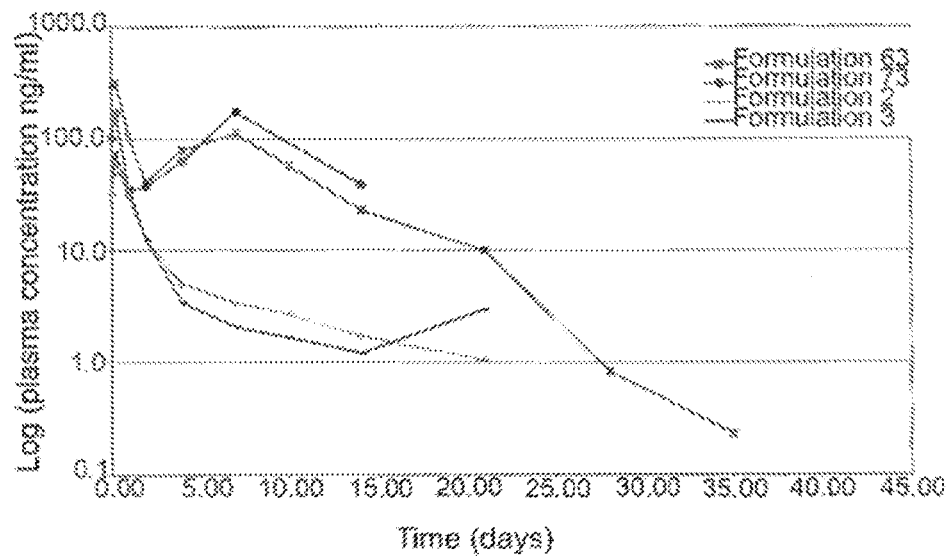
FIG. 2 shows influence of solvent type on in vivo release profile of formulations according to embodiments of the invention.

Depot gel vehicles were prepared with PLGA-502 and a solvent selected from BA, BB, EB, EtOH, NMP, and triacetin, and combinations thereof, as per procedure in Example 1. The depot gel vehicles were loaded with drug substance, in appropriate range, as per procedure in Example 3. Resulting formulations are illustrated in Table 4 below. Final homogeneous depot formulations were transferred to 3, 10 or 30 cc disposable syringes for storage or dispensing. In vivo release profiles of the formulations in Table 4 are shown in FIG. 2. $C_{max}$ to $C_{min}$ ratio and $T_{lag}$ of the formulations are shown in Table 4.

TABLE 4

| | Target content in formulation (% w/w) | | | | | | | $C_{max}/C_{min}$ | $T_{lag}$ |
|---|---|---|---|---|---|---|---|---|---|
| No. | PLGA | BA | BB | EtOH | NMP | Triacetin | EB | Drug | |
| 2[2,a,II,α,A] | 45 | 0 | 45 | 0 | 0 | 0 | 0 | 10 | 59.86 NV |
| 3[2,a,II,α,A] | 45 | 22.5 | 22.5 | 0 | 0 | 0 | 0 | 10 | 25.68 0.33 |
| 10[1,a,III,α,C] | 40 | 40 | 0 | 0 | 0 | 0 | 0 | 20 | 4.35 0.61 |
| 14[1,a,III,α,C] | 40 | 20 | 20 | 0 | 0 | 0 | 0 | 20 | 3.15 0.05 |
| 63[3,a,VII,α,C] | 43.3 | 0 | 0 | 0 | 0 | 43.3 | 0 | 13.4 | 1364.43 0.14 |
| 73[3,a,VII,α,G] | 43.3 | 0 | 0 | 0 | 0 | 0 | 43.3 | 13.4 | 5.20 N/A |

[1]= R209130, [2]= R167154, [3]= risperidone base, [4]= risperidone pamoate;
[a]= 50/50 PLGA-502 (MW = 16,000), [b]= 50/50 PLGA-502H (MW = 11,000), [c]= 50/50 PLGA (MW = 6400), [d]= 40/55/5 PCL-GA-LA (MW = ~13,500), [e]= 75/25 PLGA (MW = 14,300), [f]= 80/20 PCL-GA-LA/PVP, [g]= RG502:RG502H (1:1);0
[α]= P/S ratio of 50/50, [β]= P/S ratio of 40/60, [γ]= P/S ratio of 45/55, [δ]= P/S ratio of 60/40, [ε]= P/S ratio of 55/45;
[A]= 63-125 μm, [B]= 20-63 μm, [C]= 75-125 μm, [D]= <38 μm, [E]= micronized, [F]= as is, [G]= not applicable;
NV = no valley In Table 4 above, formulation 63 (risperidone base/PLGA/triacetin depot) has a $C_{max}$ to $C_{min}$ ratio of 1364.64. On the other hand, formulation 73 (risperidone base/PLGA/EB depot) has a $C_{max}$ to $C_{min}$ ratio of 5.20, which is significantly lower than the $C_{max}$ to $C_{min}$ ratio for formulation 63. Formulation 2 (R167154/PLGA/BB depot) has a $C_{max}$ to $C_{min}$ ratio of 59.68. n the other hand, formulation 3 (R167154/PLGA/BA/BB) has a $C_{max}$ to $C_{min}$ ratio of 25.68, which is less than half the $C_{max}$ to $C_{min}$ ratio for formulation 2. This indicates that solvent type can influence in vivo release profile of the formulation.

Example 7

This example investigates influence of polymer type on in vivo release of small molecule drugs from depot gel vehicles.

Figure 3:
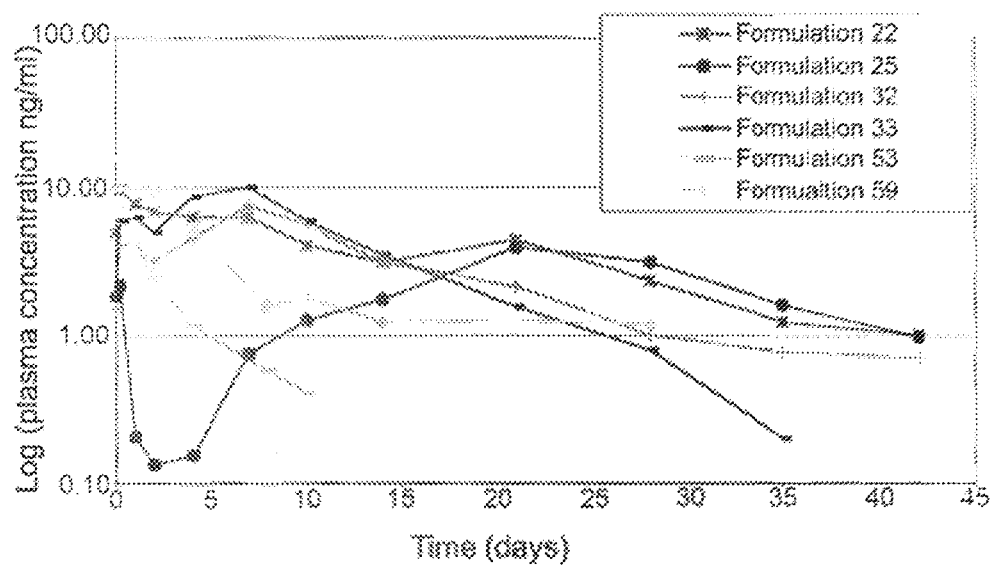
FIG. 3 shows influence of polymer type on in vivo release profile of formulations according to embodiments of the invention.

Depot gel vehicles were prepared with different polymers and loaded with 8209130, in appropriate size range, as per procedure in Example 3. Resulting formulations are illustrated in Table 5 below. Final homogeneous depot formulations were transferred to 3, 10 or 30 cc disposable syringes for storage or dispensing. Table 5 shows $C_{max}$ to $C_{min}$ ratio and $T_{lag}$ for in vivo release profiles of the formulations. FIG. 3 shows in vivo release profiles of formulations in Table 5.

TABLE 5

Target content in formulation (% w/w)

| No. | Polymer | BA | BB | Drug | $C_{max}/C_{min}$ | $T_{lag}$ |
|---|---|---|---|---|---|---|
| 22[1,a,IV,α,C] | 35 | 35 | 0 | 30 | 9.86 | 0.17 |
| 23[1,a,IV,α,E] | 35 | 0 | 35 | 30 | 6.83 | 0.17 |
| 24[1,a,IV,α,E] | 35 | 0 | 35 | 30 | 44.0 | NV |
| 25[1,c,IV,α,C] | 35 | 0 | 35 | 30 | 29.49 | 0.45 |
| 32[1,d,IV,α,C] | 35 | 0 | 35 | 30 | 10.65 | 0.12 |
| 33[1,f,IV,α,C] | 35 | 0 | 35 | 30 | 6.35 | 0.14 |
| 34[1,a,IV,α,C] | 35 | 35 | 0 | 30 | 8.75 | 0.23 |
| 35[1,c,IV,α,C] | 35 | 0 | 35 | 30 | 44.21 | NV |
| 48[1,c,IV,α,E] | 35 | 0 | 35 | 30 | 163.12 | NV |
| 53[1,e,IV,α,E] | 35 | 0 | 35 | 30 | 31.16 | 0.25 |
| 59[1,d,IV,α,C] | 35 | 0 | 35 | 30 | 6.26 | 0.07 |

[1]= R209130, [2]= R167154, [3]= risperidone base, [4]= risperidone pamoate;
[a]= 50/50 PLGA-502 (MW = 16,000), [b]= 50/50 PLGA-502H (MW = 11,000), [c]= 50/50 PLGA (MW = 6400), [d]= 40/55/5 PCL-GA-LA (MW = ~13,500), [e]= 75/25 PLGA (MW = 14,300), [f]= 80/20 PCL-GA-LA/PVP, [g]= RG502:RG502H (1:1);
[α]= P/S ratio of 50/50, [β]= P/S ratio of 40/60, [γ]= P/S ratio of 45/55, [δ]= P/S ratio of 60/40, [ε]= P/S ratio of 55/45;
[A]= 63-125 μm, [B]= 20-63 μm, [C]= 75-125 μm, [D]= <38 μm, [E]= micronized, [F]= as is, [G]= not applicable;
NV = no valley

Example 8

This example investigates influence of molecular weight of polymers on in vivo release of small molecule drugs from depot gel vehicles.

Depot gel vehicles were prepared with polymers with different molecular weights and loaded with drug substance, in appropriate size range, as per procedure in Example 3. Resulting formulations are illustrated in Table 6 below. Final homogeneous depot formulations were transferred to 3, 10 or 30 cc disposable syringes for storage or dispensing. Table 6 shows $C_{max}$ to $C_{min}$ ratio and $T_{lag}$ for in vivo release profiles of the formulations.

TABLE 6

Target content in Formulation (% w/w)

| No. | PLGA | BA | BB | Triacetin | Drug | $C_{max}/C_{min}$ | $T_{lag}$ |
|---|---|---|---|---|---|---|---|
| 10[1,a,III,α,C] | 40 | 40 | 0 | 0 | 20 | 4.35 | 0.61 |
| 11[1,a,III,α,D] | 40 | 40 | 0 | 0 | 20 | 12.06 | 0.61 |
| 12[1,a,IV,α,C] | 35 | 35 | 0 | 0 | 30 | 4.78 | 0.14 |
| 13[1,a,IV,α,D] | 35 | 35 | 0 | 0 | 30 | 5.29 | 0.36 |
| 21[1,c,III,α,C] | 40 | 40 | 0 | 0 | 20 | 48.55 | No valley |
| 25[1,c,IV,α,C] | 35 | 0 | 35 | 0 | 30 | 29.49 | 0.45 |
| 26[1,c,IV,α,D] | 35 | 0 | 35 | 0 | 30 | 41.67 | No valley |
| 48[1,c,IV,α,E] | 35 | 0 | 35 | 0 | 30 | 163.12 | No valley |
| 49[1,c,IV,δ,E] | 42 | 0 | 28 | 0 | 30 | 66.31 | 0.39 |
| 63[3,a,VII,α,C] | 43.3 | 0 | 0 | 43.3 | 13.4 | 1364.43 | 0.14 |
| 64[4,c,VIII,α,C] | 36.9 | 0 | 36.9 | 0 | 26.1 | 11.66 | No valley |
| 69[4,a,VIII,α,E] | 36.9 | 0 | 36.9 | 0 | 26.1 | 14.12 | 0.90 |
| 70[4,c,VIII,α,C] | 36.9 | 0 | 36.9 | 0 | 26.1 | 22.11 | no valley |
| 72[3,a,VII,α,G] | 43.3 | 0 | 43.3 | 0 | 13.4 | 24.48 | N/A |

[1]= R209130, [2]= R167154, [3]= risperidone base, [4]= risperidone pamoate;
[a]= 50/50 PLGA-502 (MW = 16,000), [b]= 50/50 PLGA-502H (MW = 11,000), [c]= 50/50 PLGA (MW = 6400), [d]= 40/55/5 PCL-GA-LA (MW = ~13,500), [e]= 75/25 PLGA (MW = 14,300), [f]= 80/20 PCL-GA-LA/PVP, [g]= RG502:RG502H (1:1);
[α]= P/S ratio of 50/50, [β]= P/S ratio of 40/60, [γ]= P/S ratio of 45/55, [δ]= P/S ratio of 60/40, [ε]= P/S ratio of 55/45;
[A]= 63-125 μm, [B]= 20-63 μm, [C]= 75-125 μm, [D]= <38 μm, [E]= micronized, [F]= as is, [G]= not applicable;
NV = no valley

Example 9

This example investigates influence of polymer/solvent ratios on in vivo release of small molecule drugs from depot gel vehicles.

Depot gel vehicles were prepared with different polymer/solvent ratios and loaded with drug substance, in appropriate size range, as per procedure in Example 3. Resulting formulations are illustrated in Table 7 below. Final homogeneous depot formulations were transferred to 3, 10 or 30 cc disposable syringes for storage or dispensing. Table 7 shows $C_{max}$ to $C_{min}$ ratio and $T_{lag}$ for in vivo release profiles of the formulations.

TABLE 7

Target content in Formulation (% w/w)

| No. | PLGA | BB | EtOH | Drug | $C_{max}/C_{min}$ | $T_{lag}$ |
|---|---|---|---|---|---|---|
| 22[1,a,IV,α,C] | 35 | 0 | 0 | 30 | 9.86 | 0.17 |
| 23[1,a,IV,α,C] | 35 | 35 | 0 | 30 | 6.83 | 0.17 |
| 24[1,a,IV,α,E] | 35 | 35 | 0 | 30 | 44.00 | NV |
| 25[1,c,IV,α,C] | 35 | 35 | 0 | 30 | 29.49 | 0.45 |
| 26[1,c,IV,α,D] | 35 | 35 | 0 | 30 | 41.67 | NV |
| 27[1,c,IV,β,C] | 28 | 42 | 0 | 30 | 54.16 | NV |
| 28[1,IV,β,D] | 28 | 42 | 0 | 30 | 120.74 | NV |
| 29[1,a,IV,χ,C] | 31.5 | 34.65 | 3.85 | 30 | 1.93 | NV |
| 30[1,a,IV,χ,D] | 31.5 | 34.65 | 3.85 | 30 | 7.07 | 0.29 |
| 48[1,c,IV,α,E] | 35 | 35 | 0 | 30 | 163.12 | NV |
| 49[1,c,IV,δ,E] | 42 | 28 | 0 | 30 | 66.31 | 0.39 |
| 52[1,e,IV,β,E] | 28 | 42 | 0 | 30 | 47.86 | NV |
| 53[1,e,IV,α,E] | 35 | 35 | 0 | 30 | 31.16 | 0.25 |
| 56[1,b,IV,ε,F] | 38.5 | 31.5 | 0 | 30 | 17.10 | NV |
| 65[4,c,VIII,α,E] | 36.9 | 36.9 | 0 | 26.1 | 50.87 | NV |
| 66[4,c,VIII,ε,G] | 40.6 | 33.2 | 0 | 26.1 | 38.39 | NV |
| 67[4,c,VIII,ε,G] | 33.2 | 40.6 | 0 | 26.1 | 43.55 | NV |

[1]= R209130, [2]= R167154, [3]= risperidone base, [4]= risperidone pamoate;
[a]= 50/50 PLGA-502 (MW = 16,000), [b]= 50/50 PLGA-502H (MW = 11,000), [c]= 50/50 PLGA (MW = 6400), [d]= 40/55/5 PCL-GA-LA (MW = ~13,500), [e]= 75/25 PLGA (MW = 14,300), [f]= 80/20 PCL-GA-LA/PVP, [g]= RG502:RG502H (1:1);
[α]= P/S ratio of 50/50, [β]= P/S ratio of 40/60, [χ]= P/S ratio of 45/55, [δ]= P/S ratio of 60/40, [ε]= P/S ratio of 55/45;
[A]= 63-125 μm, [B]= 20-63 μm, [C]= 75-125 μm, [D]= <38 μm, [E]= micronized, [F]= as is, [G]= not applicable;
NV = no valley

Example 10

This example investigates influence of drug loading on in vivo release of small molecule drugs from depot gel vehicles Depot gel vehicles were prepared with varying percentages of drug, in appropriate size range, as per procedure in Example 3. Resulting formulations are illustrated in Table 8 below. Final homogeneous depot formulations were transferred to 3, 10 or 30 cc disposable syringes for storage or dispensing. Table 8 shows $C_{max}$ to $C_{min}$ ratio and $T_{lag}$ for in vivo release profiles of the formulations.

TABLE 8

Target content in Formulation (% w/w)

| Formulation No. | PLGA | BA | BB | Drug | $C_{max}/C_{min}$ | $T_{lag}$ |
|---|---|---|---|---|---|---|
| 4[1,a,II,α,B] | 45 | 45 | 0 | 10 | 4.37 | 0.50 |
| 5[1,a,II,α,B] | 40 | 20 | 20 | 20 | 10.66 | 0.61 |
| 7[1,a,II,α,B] | 45 | 22.5 | 22.5 | 10 | 19.17 | 0.61 |
| 10[1,a,III,α,C] | 40 | 40 | 0 | 20 | 4.35 | 0.61 |
| 11[1,a,III,α,D] | 40 | 40 | 0 | 20 | 12.06 | 0.61 |
| 12[1,a,IV,α,C] | 35 | 35 | 0 | 30 | 4.78 | 0.14 |
| 13[1,a,IV,α,D] | 35 | 35 | 0 | 30 | 5.29 | 0.36 |
| 14[1,a,III,α,C] | 40 | 20 | 20 | 20 | 3.15 | 0.50 |
| 15[1,a,III,α,D] | 40 | 20 | 20 | 20 | 9.60 | 0.61 |
| 16[1,a,IV,α,C] | 35 | 17.5 | 17.5 | 30 | 7.16 | 0.61 |

TABLE 8-continued

| Formulation No. | Target content in Formulation (% w/w) | | | | $C_{max}/C_{min}$ | $T_{lag}$ |
|---|---|---|---|---|---|---|
| | PLGA | BA | BB | Drug | | |
| 17[1,a,IV,α,D] | 35 | 17.5 | 17.5 | 30 | 17.35 | 0.36 |
| 18[1,a,V,α,C] | 30 | 30 | 0 | 40 | 3.54 | 0.39 |

[1] = R209130, [2] = R167154, [3] = risperidone base, [4] = risperidone pamoate;
[a] = 50/50 PLGA-502 (MW = 16,000), [b] = 50/50 PLGA-502H (MW = 11,000), [c] = 50/50 PLGA (MW = 6400), [d] = 40/55/5 PCL-GA-LA (MW = ~13,500), [e] = 75/25 PLGA (MW = 14,300), [f] = 80/20 PCL-GA-LA/PVP, [g] = RG502:RG502H (1:1);
[α] = P/S ratio of 50/50, [β] = P/S ratio of 40/60, [χ] = P/S ratio of 45/55, [δ] = P/S ratio of 60/40, [ε] = P/S ratio of 55/45;
[A] = 63-125 μm, [B] = 20-63 μm, [C] = 75-125 μm, [D] = <38 μm, [E] = micronized, [F] = as is, [G] = not applicable;
NV = no valley

Example 11

This example investigates influence of drug particle size on in vivo release of small molecule drugs from depot gel vehicles.

Depot gel vehicles were prepared and loaded with drug particles in appropriate size range, as per procedure in Example 3. Resulting formulations are illustrated in Table 9 below. Final homogeneous depot formulations were transferred to 3, 10 or 30 cc disposable syringes for storage or dispensing. Table 9 shows $C_{max}$ to $C_{min}$ ratio and $T_{lag}$ for in vivo release profiles of the formulations.

TABLE 9

| Formulation No. | Target content in Formulation (% w/w) | | | | $C_{max}/C_{min}$ | $T_{lag}$ |
|---|---|---|---|---|---|---|
| | PLGA | BA | BB | Drug | | |
| 7[1,a,II,α,B] | 45 | 22.5 | 22.5 | 10 | 19.17 | 0.61 |
| 10[1,a,III,α,C] | 40 | 40 | 0 | 20 | 4.35 | 0.61 |
| 11[1,a,III,α,D] | 40 | 40 | 0 | 20 | 12.06 | 0.61 |
| 23[1,a,IV,α,C] | 35 | 0 | 35 | 30 | 6.83 | 0.17 |
| 24[1,a,IV,α,E] | 35 | 0 | 35 | 30 | 44.00 | NV |
| 25[1,a,IV,α,C] | 35 | 0 | 35 | 30 | 29.49 | 0.45 |
| 26[1,c,IV,α,D] | 35 | 0 | 35 | 30 | 41.67 | NV |
| 64[4,c,VIII,α,C] | 36.9 | 0 | 36.9 | 26.1 | 11.66 | NV |
| 65[4,c,VIII,α,E] | 36.9 | 0 | 36.9 | 26.1 | 50.87 | NV |
| 66[4,c,VIII,ε,G] | 40.6 | 0 | 33.2 | 26.1 | 38.39 | NV |
| 72[3,a,VII,α,G] | 43.3 | 0 | 43.3 | 13.4 | 24.48 | N/A |

[1] = R209130, [2] = R167154, [3] = risperidone base, [4] = risperidone pamoate;
[a] = 50/50 PLGA-502 (MW = 16,000), [b] = 50/50 PLGA-502H (MW = 11,000), [c] = 50/50 PLGA (MW = 6400), [d] = 40/55/5 PCL-GA-LA (MW = ~13,500), [e] = 75/25 PLGA (MW = 14,300), [f] = 80/20 PCL-GA-LA/PVP, [g] = RG502:RG502H (1:1);
[α] = P/S ratio of 50/50, [β] = P/S ratio of 40/60, [χ] = P/S ratio of 45/55, [δ] = P/S ratio of 60/40, [ε] = P/S ratio of 55/45;
[A] = 63-125 μm, [B] = 20-63 μm, [C] = 75-125 μm, [D] = <38 μm, [E] = micronized, [F] = as is, [G] = not applicable;
NV = no valley

Example 12

Figure 4:
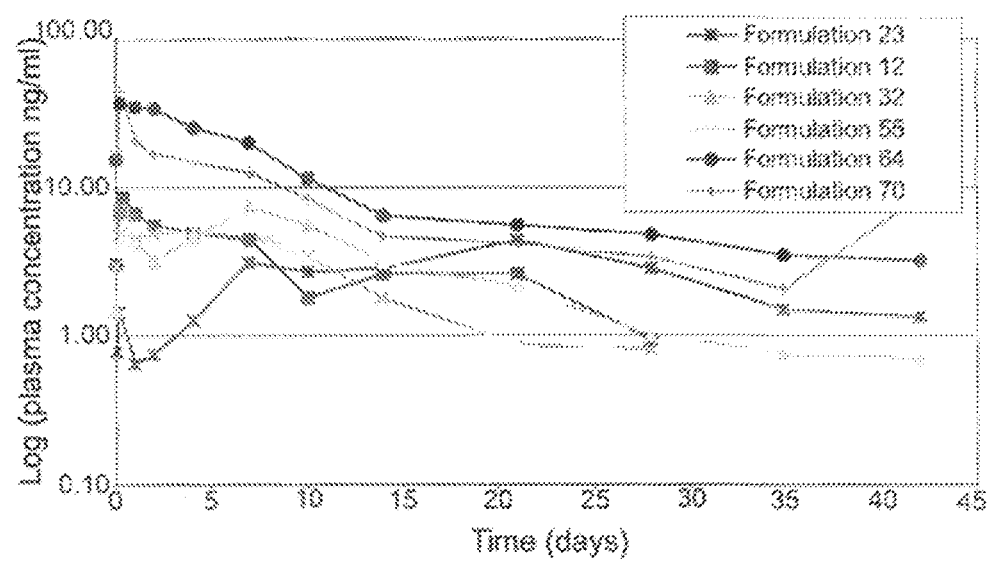
FIG. 4 shows formulations having near zero-order release profiles according to embodiments of the invention.

A formulation is described as near zero-order if the ratio of $C_{max}$ to $C_{min}$ is less than 200, preferably less than 50, more preferably less than 30. $T_{lag}$ in release of formulation is preferably less than 0.2. Formulations that do not show $C_{valley}$ do not exhibit lag. Table 10 shows a number of formulations that exhibited the characteristic near zero-order release. FIG. 4 shows in vivo release profiles of selected formulations in Table 10.

TABLE 10

| Formulation No. | Target content in Formulation (% w/w) | | | | | $C_{max}/C_{min}$ | $T_{lag}$ |
|---|---|---|---|---|---|---|---|
| | Polymer | BA | BB | EtOH | Drug Particles | | |
| 12[1,a,IV,α,C] | 35 | 35 | 0 | 0 | 30 | 4.78 | 0.14 |
| 22[1,a,IV,α,C] | 35 | 35 | 0 | 0 | 30 | 9.86 | 0.17 |
| 23[1,a,IV,α,C] | 35 | 0 | 35 | 0 | 30 | 6.83 | 0.17 |
| 29[1,a,IV,χ,C] | 31.5 | 0 | 34.65 | 3.85 | 30 | 1.93 | NV |
| 32[1,a,IV,α,C] | 35 | 35 | 0 | 0 | 30 | 10.65 | 0.12 |
| 33[1,f,IV,α,C] | 35 | 0 | 35 | 0 | 30 | 6.35 | 0.14 |
| 35[1,e,IV,α,C] | 35 | 0 | 35 | 0 | 30 | 44.21 | NV |
| 55[1,e,IV,α,C] | 35 | 0 | 35 | 0 | 30 | 6.33 | 0.11 |
| 56[1,b,IV,ε,F] | 38.5 | 0 | 31.5 | 0 | 30 | 17.10 | NV |
| 60[1,c,VI,α,C] | 25 | 0 | 25 | 0 | 50 | 12.90 | 0.07 |
| 61[1,c,IV,α,C] | 35 | 0 | 35 | 0 | 30 | 26.53 | 0.11 |
| 64[4,c,VIII,α,C] | 36.9 | 0 | 36.9 | 0 | 26.1 | 11.66 | NV |
| 70[4,c,VIII,α,C] | 36.9 | 0 | 36.9 | 0 | 26.1 | 22.11 | NV |

[1] = R209130, [2] = R167154, [3] = risperidone base, [4] = risperidone pamoate;
[a] = 50/50 PLGA-502 (MW = 16,000), [b] = 50/50 PLGA-502H (MW = 11,000), [c] = 50/50 PLGA (MW = 6400), [d] = 40/55/5 PCL-GA-LA (MW = ~13,500), [e] = 75/25 PLGA (MW = 14,300), [f] = 80/20 PCL-GA-LA/PVP, [g] = RG502:RG502H (1:1);
[α] = P/S ratio of 50/50, [β] = P/S ratio of 40/60, [χ] = P/S ratio of 45/55, [δ] = P/S ratio of 60/40, [ε] = P/S ratio of 55/45;
[A] = 63-125 μm, [B] = 20-63 μm, [C] = 75-125 μm, [D] = <38 μm, [E] = micronized, [F] = as is, [G] = not applicable;
NV = no valley While the invention has been described with respect to a limited number of embodiments, those skilled in the art, having benefit of this disclosure, will appreciate that other embodiments can be devised which do not depart from the scope of the invention as disclosed herein.

What is claimed is:

1. An injectable pharmaceutical composition comprising from about 10 wt % to about 30 wt % of risperidone base suspended in a gel comprising: (i) from about 40 wt % to about 60 wt % of a copolymer of lactic acid and glycolic acid, wherein the lactic acid to glycolic acid monomer ratio is from about 100:0 to about 60:40, and wherein the copolymer has a number average molecular weight from about 5,000 Daltons to about 30,000 Daltons, and (ii) benzyl benzoate, benzyl alcohol, ethyl benzoate, triacetin, N-methyl-2-pyrrolidone, or a combination of two or more thereof.

2. The composition of claim 1, wherein the gel consists of (i) and (ii).

3. An injectable pharmaceutical composition comprising from about 1 wt % to about 50 wt % of risperidone base suspended in a gel comprising: (i) from about 5 wt % to about 80 wt % of a copolymer of lactic acid and glycolic acid, and (ii) benzyl benzoate, benzyl alcohol, ethyl benzoate, triacetin, N-methyl-2-pyrrolidone, or a combination of two or more thereof.

4. The composition of claim 3, comprising from about 5 wt % to about 40 wt % of risperidone base.

5. The composition of claim 4, comprising from about 5 wt % to about 30 wt % of risperidone base.

6. The composition of claim 5, comprising from about 10 wt % to about 30 wt % of risperidone base.

7. The composition of claim 3, wherein the gel comprises: (i) from about 20 wt % to about 70 wt % of a copolymer of lactic acid and glycolic acid, and (ii) benzyl benzoate, benzyl alcohol, ethyl benzoate, triacetin, N-methyl-2-pyrrolidone, or a combination of two or more thereof.

8. The composition of claim 7, wherein the gel comprises: (i) from about 40 wt % to about 60 wt % of a copolymer of lactic acid and glycolic acid, and (ii) benzyl benzoate, benzyl alcohol, ethyl benzoate, triacetin, N-methyl-2-pyrrolidone, or a combination of two or more thereof.

9. The composition of claim 3, wherein the lactic acid to glycolic acid monomer ratio in the copolymer is from about 100:0 to 60:40.

10. The composition of claim 9, wherein the lactic acid to glycolic acid monomer ratio in the copolymer is from about 100:0 to 75:25.

11. The composition of claim 3, wherein the copolymer has a number average molecular weight from about 1,000 Daltons to about 120,000 Daltons.

12. The composition of claim 11, wherein the copolymer has a number average molecular weight from about 5,000 Daltons to about 30,000 Daltons.

13. The composition of claim 3, wherein the gel consists of (i) and (ii).

14. An injectable pharmaceutical composition comprising risperidone base suspended in a gel comprising: (i) a copolymer of lactic acid and glycolic acid, and (ii) benzyl benzoate, benzyl alcohol, ethyl benzoate, triacetin, N-methyl-2-pyrrolidone, or a combination of two or more thereof.

15. A method of administering risperidone base to a subject in need thereof, the method comprising subcutaneously injecting the composition of claim 1 into the subject once per month.

16. A method of administering risperidone base to a subject in need thereof, the method comprising subcutaneously injecting the composition of claim 3 into the subject once per month.

17. A method of administering risperidone base to a subject in need thereof, the method comprising subcutaneously injecting the composition of claim 14 into the subject once per month.

18. A syringe comprising the composition of claim 1.

19. A syringe comprising the composition of claim 3.

20. A syringe comprising the composition of claim 14.

* * * * *